(12) United States Patent
Boone et al.

(10) Patent No.: US 8,541,242 B2
(45) Date of Patent: Sep. 24, 2013

(54) DEVICE AND METHOD FOR DETECTION OF ANALYTES

(75) Inventors: James H. Boone, Christiansburg, VA (US); David M. Lyerly, Radford, VA (US); Tracy D. Wilkins, Riner, VA (US)

(73) Assignee: Techlab, Inc., Blacksburg, VA (US)

(*) Notice: Subject to any disclaimer, the term of this patent is extended or adjusted under 35 U.S.C. 154(b) by 112 days.

(21) Appl. No.: 13/172,474

(22) Filed: Jun. 29, 2011

(65) Prior Publication Data
US 2011/0318240 A1    Dec. 29, 2011

Related U.S. Application Data

(62) Division of application No. 11/720,142, filed as application No. PCT/US2005/042902 on Nov. 23, 2005.

(60) Provisional application No. 60/630,152, filed on Nov. 24, 2004.

(51) Int. Cl.
| | |
|---|---|
| *G01N 21/75* | (2006.01) |
| *G01N 21/77* | (2006.01) |
| *G01N 33/53* | (2006.01) |
| *G01N 33/542* | (2006.01) |
| *G01N 33/554* | (2006.01) |

(52) U.S. Cl.
USPC ........ 436/169; 435/4; 435/5; 435/6.1; 435/6.15; 435/6.19; 435/7.1; 435/7.2; 435/7.22; 435/7.31; 435/7.32; 435/7.8; 435/7.9; 435/7.92; 435/26; 435/29; 435/39; 435/174; 435/287.2; 436/164; 436/168; 436/170; 436/501; 436/536

(58) Field of Classification Search
None
See application file for complete search history.

(56) References Cited

U.S. PATENT DOCUMENTS

| | | | |
|---|---|---|---|
| 5,037,736 A | | 8/1991 | Freitag |
| 5,185,127 A | * | 2/1993 | Vonk .......................... 422/408 |
| 5,232,663 A | | 8/1993 | Wilk et al. |
| 5,415,994 A | | 5/1995 | Imrich et al. |
| 5,418,171 A | | 5/1995 | Kimura et al. |
| 5,602,040 A | * | 2/1997 | May et al. ...................... 436/514 |
| 5,731,162 A | | 3/1998 | Gatti |
| 5,770,460 A | | 6/1998 | Pawlak et al. |
| 5,965,373 A | | 10/1999 | Zimmermann et al. |
| 5,965,375 A | | 10/1999 | Valkirs |

(Continued)

FOREIGN PATENT DOCUMENTS

| | | |
|---|---|---|
| EP | 0529852 | 3/1993 |
| EP | 1072578 | 1/2011 |

(Continued)

OTHER PUBLICATIONS

Non-Final Action Dated Nov. 30, 2009 re U.S. Appl. No. 11/720,142.

(Continued)

*Primary Examiner* — Ja'Na Hines
(74) *Attorney, Agent, or Firm* — Shook, Hardy & Bacon L.L.P.

(57) ABSTRACT

The present invention provides assays and devices for detection of substances in liquid samples. The assays and devices utilize passive diffusion between a porous material and a porous membrane containing a specific binding pair member to enable detection of the substance of interest.

11 Claims, 15 Drawing Sheets

(56) References Cited

U.S. PATENT DOCUMENTS

| | | | |
|---|---|---|---|
| 5,980,640 | A | 11/1999 | Nurmi et al. |
| 5,989,924 | A | 11/1999 | Root et al. |
| 6,106,732 | A | 8/2000 | Johnston et al. |
| 6,303,389 | B1 | 10/2001 | Levin et al. |
| 6,593,085 | B1 | 7/2003 | Barnett |
| 6,766,817 | B2 | 7/2004 | da Silva |

FOREIGN PATENT DOCUMENTS

| | | |
|---|---|---|
| GB | 1287509 | 8/1972 |
| GB | 1481846 | 8/1977 |
| JP | 2002-286716 | 5/2011 |
| WO | 94/06012 | 5/1994 |
| WO | WO9959426 | 11/1999 |
| WO | WO2004103939 | 12/2004 |

OTHER PUBLICATIONS

Final Office Action Dated Mar. 15, 2010 re U.S. Appl. No. 11/720,142.
Non-Final Office Action Dated Feb. 10, 2011 re U.S. Appl. No. 11/720,142.
International Search Report re WO 2004/103939 dated May 10, 2004.
JP Office Action dated Apr. 26, 2011.
Final Office Action Dated Aug. 17, 2011 re U.S. Appl. No. 11/720,142.
Non-Final Office Action mailed Feb. 29, 2012 regarding U.S. Appl. No. 11/720,142 29 pages.
Notice of Allowance mailed Sep. 18, 2012 re U.S. Appl. No. 11/720,142, 21 pgs.
Canada Examiner's Report dated Apr. 12, 2012 regarding PCT/Canada Appln. 2,588,420 5 pages.
Japanese Abstract JPH04232861 to Hirokazu dated Aug. 21, 1992.
Japanese Abstract JP2001296297 to Kenji dated Dec. 21, 2001.
Japanese Abstract JPH07046107 to May et al., dated May 17, 1995.
Japanese Examiner's Report dated Feb. 14, 2012 regarding Japanese Pat App 2007-543567.
European Supplemental Search Report dated Oct. 5, 2011 re EP 05852268.

\* cited by examiner

DEVICE AND METHOD FOR DETECTION OF ANALYTES

CROSS-REFERENCE TO RELATED APPLICATIONS

This application is a divisional application of co-pending U.S. patent application Ser. No. 11/720,142 filed May 24, 2007, which claims priority to PCT/US05/042902, filed Nov. 23, 2005, which claims priority to U.S. provisional application 60/630,152, filed Nov. 24, 2004, each of which is hereby incorporated herein by reference in its entirety.

BACKGROUND OF THE INVENTION

1. Field of the Invention

The present invention relates to devices and methods for detecting substances that are present in liquids. In particular, the invention relates to devices and methods for detecting small molecules, such as chemicals or biological products, that are present in liquid samples derived from body tissues or the environment.

2. Description of Related Art

There are various types of devices and methods available in the art for detecting substances in samples. A large segment of the field utilizes membrane-bound molecules that specifically bind to the substance of interest or to a molecule that is bound to the substance of interest. The two main types of devices and methods are generally referred to as lateral flow and flow through. These tests are generally relatively rapid (less than 1 hour to detect a substance) and sensitive (ng/ml range).

In a flow through device, a sample is pulled through a membrane by capillary action and the substance (analyte, antigen, etc.) is retained on the membrane by binding to a specific antibody, receptor, peptide, etc. The binding is detected by binding of a second antibody or other molecule that is coupled to either an enzyme (e.g., horseradish peroxidase), a colloidal particle (e.g., gold sol), or various other labels and particles (e.g., fluorescent labels, paramagnetic beads). The binding occurs very rapidly as the sample is pulled through the membrane and the membrane is then washed (buffer is pulled through the membrane) and the detection reagent is added. The result is a detectable signal, such as a spot of color, a line, a plus sign, etc.

In a lateral flow device, the sample wicks across a thin membrane by capillary action and flows through a line of a reagent, such as an antibody or other binding component (binding peptides, receptors, etc.). In certain versions, the analyte has already been bound by an antibody with a colored particle attached (e.g., gold sol, blue dextran bead, etc). This complex of antigen and antibody-gold is bound by the reagent line and a colored line appears. There is no washing involved and no liquid reagents are used, except that the sample may be diluted in a buffered solution before it is placed onto the conjugate pad which contains the antibody-gold sol as a dried reagent.

In other versions of the lateral flow device, the sample is usually mixed with a buffer containing an antibody-enzyme conjugate. This is placed onto the membrane, and wicking occurs by lateral flow along the thin membrane. A line is not immediately visible because a reagent must be added. Usually this is a colorless chemical that is converted into an insoluble colored precipitate by the enzyme (e.g., horseradish peroxidase, etc.). This version must be washed to leach away the unbound enzyme, so there is an absorbent pad at each end of the membrane and the membrane is typically more porous than that used for gold-sol lateral flow (this facilitates washing).

Although the devices and methods currently available for detecting substances in liquid samples are suitable and effective for detecting most substances of interest, there is a need for new devices and methods having improved speed, sensitivity, and ease of use.

BRIEF SUMMARY OF THE INVENTION

The present invention addresses needs in the art by providing a device and method for rapidly detecting substances in liquid samples, which are sensitive and easy to use. The present device and method enable clinicians to rapidly detect organisms, biological products such as toxins or other biological materials such as proteins, nucleic acids (DNA, RNA), and polysaccharides, and drugs or other man-made chemicals, in tissue samples. By tissue samples, it is meant any composition that contains biological material originating from one or more animal cells or tissues (including the blood system), including, but not limited to, tissues (e.g., whole blood or fractions thereof, tumor tissue, urine, excrement or excretion products, such as feces, diarrhea) of humans and animals (e.g., veterinarian samples from farm animals or companion animals, meat intended for human consumption, such as hamburger, steak, bacon, eggs, prepared food). It thus includes liquid or semi-liquid samples of biological materials that do not need dilution prior to use in the method or with the device of the invention. It likewise permits the detection of biological or chemical substances in environmental samples, including surface soil, subsurface soil, rock, and water, and surface water. In addition, it can be used to detect airborne substances where such substances can be captured and dissolved in a liquid. For example, aerosols can be solubilized or otherwise combined with a liquid to create a liquid composition, which can be used as a sample for detection of a substance of interest.

In general, the method of the invention uses diffusion of a substance through a membrane to permit detection, either directly or indirectly, of that substance by a specific binding pair member. Unlike detection methods in current use, which rely on passing, in a unidirectional manner, a substance over or through a membrane containing a specific binding pair member for the substance, the present methods do not rely on such unidirectional passing of substance over or through a membrane. Rather, the present methods rely on simple diffusion of a substance through, around, over, across, and about a membrane to detect the substance, with no uniform directionality of movement with respect to the membrane being necessary. Surprisingly, it has been found that simple diffusion through, around, over, across, and/or about a membrane containing a specific binding pair member for a substance of interest is sufficient for rapid and sensitive detection of the substance.

Accordingly, the method of the invention generally comprises providing a liquid containing, or suspected of containing, a substance of interest; applying the liquid to a porous material, such as a pad, in a sufficient amount to at least partially wet the porous material; contacting the porous material with a porous membrane comprising a specific binding pair member that is capable of binding, either directly or indirectly, the substance of interest; and detecting the presence or absence of a complex comprising the specific binding pair member and the substance of interest, where the presence of such a complex indicates the presence of the substance in the liquid.

Broadly speaking, the device of the invention comprises any configuration of components that permit practice of the method of the invention. More specifically, the device of the invention comprises any configuration of components that permit a liquid sample containing, or suspected of containing, a substance of interest to be retained in a pre-defined area or region of the device, where the area or region comprises a porous membrane comprising a specific binding pair member that is specific, either directly or indirectly, for the substance. Within this area, the sample can diffuse across, through, etc. the membrane.

In its most basic form, the device of the invention comprises (a) a receptacle comprising a porous material or pad that is capable of absorbing and transmitting a liquid, and (b) a porous membrane that comprises a specific binding pair member that is specific for a substance to be detected. The receptacle and porous membrane are each shaped to permit the porous membrane to be in direct contact with the porous material over at least a portion of the porous membrane that comprises the specific binding pair member. In embodiments, the pad and membrane are in direct contact with each other over at least a portion of the porous membrane that comprises the specific binding pair member. The device can comprise a container containing the receptacle. The device can comprise a holder for the porous membrane. In embodiments, the device comprises the container and holder in contact with each other, the contact between the two elements causing the porous membrane and the porous material to be in direct contact with each other over at least a portion of the porous membrane that comprises the specific binding pair member. In addition, the device can comprise a sample application pad and a wash solution receiving pad.

BRIEF DESCRIPTION OF THE DRAWINGS

The accompanying Figures, which are incorporated in and constitute a part of this specification, illustrate several embodiments of the invention and together with the written description serve to explain certain principles of the invention. The Figures provide details of certain embodiments of the invention in order to help better explain various features of the depicted embodiments. Because the Figures depict exemplary embodiments of the invention only, they are not to be construed as limiting the scope of the invention to the particular details depicted in them.

DETAILED DESCRIPTION OF THE INVENTION

Figure 1:
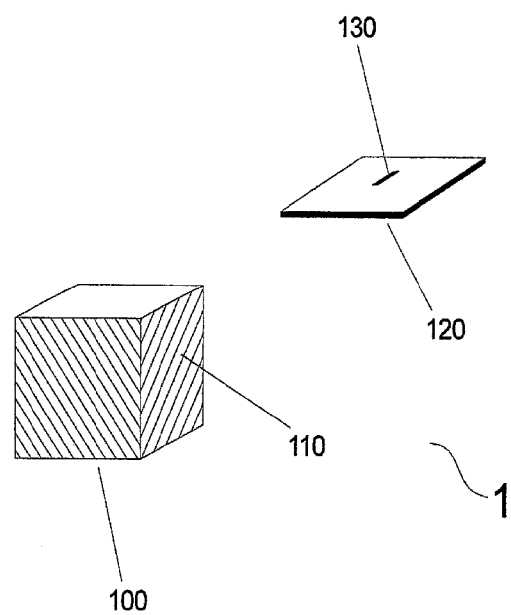
FIG. 1 is a perspective view of a basic configuration of the device of the invention, comprising a porous membrane and a receptacle.

Before proceeding with a description of the invention and various embodiments, certain terms used herein will be defined at this point. Other terms used herein are used in accordance with their normal definition in the art or are defined at some other point herein.

As used herein, a substance is anything, including, but not necessarily limited to, simple, natural organic molecules such as sugars and short-chain acids; complex biological molecules such as peptides, nucleic acids (e.g., DNA, RNA, PNA), and polysaccharides; and man-made (whether though manipulation of biological processes or through chemical syntheses) molecules such as drugs, industrial agents, pesticides, and defoliants. Thus, a substance can be a drug, hormone (such as one present during pregnancy or ovulation), protein (including antibody), toxin, DNA (including single-stranded DNA), RNA (including double-stranded RNA), virus or viral protein or nucleic acid, bacterium or bacterial protein or nucleic acid, polysaccharide, pollutant, and the like. It can thus be a bacterial or viral pathogen or a prokaryotic or eukaryotic parasite.

For example, the substance can be a living organism or virus, or any part thereof, including, but not limited to, macromolecules. Thus, the substance can be a gram positive or gram negative procaryotic organism, such as a *Eubacterium* or Archaea. Non-limiting examples of bacterial organisms include *Clostridium* species, such as *C. difficile, C. tetani, C. botulinum*, and *C. perfringens; Escherichia coli*; a *Salmonella* species, such as *Salmonella typhimurium*, and *Salmonella typhi*; a *Bacillus* species, such as *Bacillus anthracis* and *B. cereus*; a *Staphylococcus* species, such as *S. aureus* and *S. epidermidis*; a *Streptococcus* species, such as *S. pyogenes, S. mutans*, and *S. pneumoniae*; a *Neisseria* species, such as *N. meningitidis* and *N. gonorrhoeae*; a *Haemophilus* species, such as *H. influenzae*; a *Bordetella* species, such as *B. pertussis, B. parapertussis*, and *B. bronchiseptica*, a *Listeria* species, such as *L. monocytogenes*; a *Corynebacterium* species, such as *C. diphtheriae*, and *C. pseudotuberculosis*; a *Mycobacterium* species, such as *M. tuberculosis, M. Bovis, M. scrofulaceum, M. avium-intracellulare*, and *M. leprae*; an *Actinomycetes* species; a *Klebsiella* species, such as *K. pneumoniae*; a *Serratia* species, such as *S. marcescens*; a *Proteus* species, such as *P. mirabilis* and *P. vulgaris*; a *Shigella* species, such as *S. flexneri*; a *Vibrio* species, such as *V. cholerae*; a *Pseudomonas* species, such as *P. aeruginosa*; a *Yersinia* species, such as *Y. pestis*; a *Francisella* species, such as *F. tularensis*; a *Brucella* species, such as *B. abortus, B. suis*, and *B. canis*; a *Treponema* species, such as *T. pallidum*; a *Borrelia* species, such as *B. burgdorferi*; a *Campylobacter* species, such as *C. jejuni* and *C. fetus*; a *Legionella* species, such as *L. pneumophila*; a *Rickettsiae* species; a *Chlamydia* species, such as *C. trachomatis* and *C. psittaci*; and a *Mycoplasma* or *Acholeplasma* species.

Of course, the substance can be a virus or any part thereof. Non-limiting examples of viruses include immunodeficiency viruses, such as human immunodeficiency viruses (e.g., HIV-1, HIV-2, HIV-O); hepatitis viruses, such as hepatitis C virus (HCV), and hepatitis B virus (HBV); papilloma viruses, such as human papilloma virus (HPV); and any other virus associated with human or animal disease.

Because the substance can be any portion of a living or non-living entity, the substance can be a protein or portion thereof associated with a neurodegenerative disease, such as Alzheimer's disease or a transmissible spongiform encephalopathy, such as a prion disease. Thus, the substance can be a prion protein or portion thereof.

Other non-limiting examples of substances include parasites or any portion thereof. Thus, substances can be all or part of a *Giardia* species, a *Cryptosporidium* species, or an *Entamoeba* species.

As used herein, a specific binding pair member is a substance that specifically binds, either directly or indirectly, to another substance. Thus, together, the specific binding pair member and the other substance create a pair of substances. Because the two substances specifically bind each other, both can be considered specific binding pair members for each other. However, for clarity purposes, one will be referred to as the specific binding pair member and the other as a substance to which it binds. Examples of specific binding pair members include, but are not limited to, antibody-antigen pairs (including, but not limited to, antibody-antibody pairs where one antibody specifically binds another antibody), enzyme-substrate pairs, complementary nucleic acid pairs, protein-nucleic acid pairs (such as DNA and DNA-binding protein pairs, including, but not limited to, an operator sequence and a transcription factor), and protein-protein pairs (including, but not limited to, subunits of a multi-subunit protein). Examples also include artificial peptides that bind to a target, receptors, ligands, artificial antibodies (e.g., single chain antibodies, recombinant antibodies, antibodies containing just the antigen binding region, bacterially produced antibodies or antibody parts). Other exemplary binding pair members include two or more nucleic acids that contain regions of complementarity, either over a portion or the entirety of one or more of the nucleic acids, and which can specifically bind or hybridize under appropriate conditions. The invention is directed to detecting substances in a sample. However, it should not be assumed that the substances is necessarily one of the specific binding pair members. Rather, a specific binding pair member can be a substance that specifically reacts with another specific binding pair member, and at the same time binds to a substance of interest in the sample (e.g., an antibody that binds to a substance of interest and at the same time is specifically bound by another antibody). As used herein, disclosure of a specific binding pair member (e.g., an antibody) binding to a substance of interest in a sample includes not only direct binding of the specific binding pair member to the particular substance, but to another specific binding pair member that is bound to the substance. For example, a specific binding pair may be biotin and avidin or streptavidin.

Rapid test devices and methods currently used in the art work because they force a substance (e.g., an antigen) and a specific binding pair member (e.g., an antibody) to come together, either by sucking the sample through a membrane coated with the antibody (flow through devices and methods) or by pulling it along a membrane by capillary action (lateral flow devices and methods). The present invention does not rely on either of these principles. According to the present invention, a porous membrane comprising the specific binding pair member simply needs to contact a porous material (e.g., a pad) that contains the substance. Simple diffusion in and out of the porous material and membrane causes the substance and specific binding pair member to come into contact. That the present invention provides a rapid and sensitive test for substances in samples is surprising because it is widely held that simple diffusion is not sufficient for detection of a substance, much less detection with high sensitivity by way of binding to a specific binding pair member associated with a solid support, such as a membrane. Indeed, the present invention provides exceptionally sensitive detection of substances at times comparable to those used for lateral flow or flow through devices and methods. Because the sample does not have to be applied directly to, and does not necessarily flow directly through, the membrane comprising the specific binding pair member, the test also can be used on samples that clog the membranes of other rapid tests.

In a first aspect, the present invention provides a method of detecting a substance that is present in a liquid sample. The method of the invention uses passive diffusion of a substance from a receptacle comprising a porous material, such as a pad, to a porous membrane. Such diffusion permits detection, either directly or indirectly, of the substance by a specific binding pair member associated with the porous membrane. Unlike common detection methods in current use, which rely on passing, in a unidirectional manner, a substance across or through a membrane containing a specific binding pair member for the substance, the present methods do not rely on such unidirectional movement of the substance. Rather, the present methods rely on simple diffusion of a substance through, around, over, across, and/or about a membrane to detect the substance, with no single directionality of movement with respect to the membrane being necessary. Surprisingly, it has been found that simple diffusion through, around, over, across, and about a membrane containing a specific binding pair member for a substance of interest is sufficient for rapid and sensitive detection of the substance.

The method of the invention generally comprises providing a liquid comprising or suspected of comprising a substance of interest; applying the liquid to a porous material in a sufficient amount to at least partially wet the porous material; contacting the porous material with a porous membrane comprising a specific binding pair member that is capable of binding, either directly or indirectly, the substance of interest; maintaining the wetted porous material and the porous membrane in contact for a sufficient amount of time for the porous membrane to become wetted at least in the area comprising the specific binding pair member; and detecting the presence or absence of a complex comprising the specific binding pair member and the substance of interest, where the presence of such a complex indicates the presence of the substance in the liquid.

The liquid comprising or suspected of comprising a substance of interest can be provided in any number of ways. For example, it can be provided in the form that it was isolated from its natural environment (e.g., whole blood, urine, diarrheal feces, and stream, river, or lake water can be used directly as isolated). Thus, it can be an undiluted sample. Alternatively, it can be provided in a form after having been treated to remove one or more components (e.g., the liquid portion of blood and feces can be used after centrifugation, filtration, or precipitation of solid matter). In addition, where the original sample is solid or substantially solid, a liquid, such as water, may be added to the sample to provide liquid characteristics. Other handling or manipulation of the liquid can be performed prior to or at the time of providing the liquid. Any handling or manipulation may be used as long as it does not render the sample incapable of use in the method of the invention or in the device of the invention.

The liquid can be any liquid, including, but not limited to, water or compositions containing water, such as biological tissues, extracts of biological tissues, and biological excretions; organic solvents or compositions containing organic solvents; and combinations of water and organic solvents or combinations of aqueous and/or organic solvent compositions. For example, the liquid can be a biological fluid, such as blood or a portion of blood, urine, feces, saliva, sputum, mucous, semen, or homogenized tissue. It thus can be a homogenized sample of human or animal tissue, such as homogenized meat (e.g., hamburger, lamb, pork, chicken, fish, egg). It also may be an extract of a solid specimen, such as an aqueous extract of a fecal sample or of a consumable meat sample. Where the tissue to be analyzed is not suitable for liquification as isolated, water or another liquid may be added to the tissue to provide suitable liquid characteristics. Because the present invention is suitable for detection of substances in liquids having a wide range of viscosities, the present method is suitable for detecting substances present in liquid or semi-liquid compositions.

Where necessary, the amount or concentration of the substance to be detected within the liquid, if present, can be adjusted to achieve satisfactory detection. Adjustment can be accomplished by dilution with a liquid that is compatible with the liquid sample and the components of the device of the invention, or can be accomplished by concentration of the substance within the liquid sample using any suitable concentration technique, including, but not limited to, centrifugation, filtration, evaporation, affinity purification, or the like. In general, the substance to be detected is present in the sample in nanogram (ng) to microgram (ug) amounts.

Additional components may also be added to the liquid prior to, or at the time of, applying of the liquid to the porous material. Anything that does not interfere substantially with the ability of the specific binding pair member to specifically complex with the substance or a specific binding pair member that binds to the substance may be added to the liquid. In embodiments, a label that specifically interacts with the substance, if present, is added to the liquid prior to or at the time of applying the liquid to the porous material. For example, an antibody that specifically binds to the substance of interest can be added to the liquid prior to applying the liquid to the porous material. The antibody may be labeled with a moiety that can be detected, either directly or through the use of ancillary materials. Exemplary moieties include, but are not limited to, alkaline phosphatase, horseradish peroxidase, fluorescent compounds, paramagnetic beads, gold or other metals, latex beads, avidin (streptavidin), and biotin. Thus, in embodiments, an antibody conjugate that specifically binds to the substance of interest is added to the liquid sample prior to or at the time of applying the liquid sample to the porous material/pad.

The liquid is applied to the porous material in a sufficient amount to at least partially wet the porous material. It is preferred that a sufficient amount of liquid is applied to wet that portion of the porous material that is in contact with the porous membrane at the region where the specific binding pair member is located. In preferred embodiments, the entire porous material or substantially the entire porous material is wetted. In embodiments where the porous material extends beyond the area covered by the porous membrane, it is preferred that a sufficient amount of liquid is applied to wet the porous membrane at least at the region where the specific binding pair member is located.

Applying can be accomplished by any suitable technique, including, but not limited to, dipping of the porous material into the liquid, pouring the liquid onto the porous material, placing the porous material in the path of a stream of liquid (e.g., dipping into a flowing river, inserting into a stream of urine), dropping the liquid onto the porous material (e.g., with an eye dropper or pipette), and smearing a semi-liquid sample onto the porous material. Applying can be accomplished by direct application to the porous material or to another porous material in contact with the porous material. Likewise, it can be accomplished by applying to an area of the porous material that is physically distant from another site, and permitting the liquid to migrate through the porous material to the other site.

In practice of the invention, at least a portion of the liquid that is applied should be present at a site directly in contact with a portion of the membrane comprising a specific binding pair member. Thus, the liquid can be applied to a portion of the porous material adjacent the area where the porous membrane is in contact with the porous material or is intended to be in contact with the porous material (e.g., in the reaction pad area, which includes the detection area or site) or can be applied at a site distal to the reaction pad area, and allowed to migrate to that area. When applied at a distant site, due to the porosity of the material, the liquid will travel through the porous material from the site of application to the site of detection of the presence of the substance (i.e., to the site on the porous material where the porous membrane is in contact).

Applying the liquid at a site away from the site of detection can permit filtration of the liquid before detection of the substance. That is, the porous material can act not only to transport the liquid and its components to the site of detection, but can also act to block or retard migration of certain components present in the sample, thus effectively acting as a filtration system that permits substances of a certain size only to migrate to the detection area. Numerous different porous materials are available, having various different pore sizes, and one may select the appropriate material and pore size to effectively filter out unwanted components in the liquid. For example, when applying a liquid comprising feces, one may want to filter out large particles, such as undigested or partially digested food or bacteria. In such a situation, one may select a porous material that has a pore size that blocks or significantly retards migration of these relatively large components while permitting smaller components, such as bacterial proteins, nucleic acids, extracellular blood proteins, or the like, to migrate through the material essentially unimpeded.

The method of the invention also comprises contacting the porous material with a porous membrane comprising a specific binding pair member that is capable of binding, either directly or indirectly, the substance of interest. Contacting of the porous material and the porous membrane can occur prior to or after applying the liquid to the porous material. Furthermore, it is not relevant whether the material or the membrane is caused to move in order to effect contact. Contacting encompasses physical movement of either or both the porous material and porous membrane to achieve contact.

Although not necessary, typically when the liquid is to be applied to a porous material at a site away from the site of detection of the presence of the substance, the porous material and porous membrane are contacted with each other prior to applying the liquid. On the other hand, when the liquid is applied to the porous material at or very near the site where the porous material and porous membrane make contact, the liquid is typically applied before the membrane and material are contacted.

It has been found that direct contact of the membrane at the site where the specific binding pair member is located with a porous material through which a substance of interest can travel improves the sensitivity and speed of the method of the invention. Therefore, it is preferred that the porous membrane and porous material are in contact at this site, or at least over a portion of this site. Contact between the porous material and porous membrane should be continuous contact over at least the portion of the membrane where the specific binding pair member is located, or over a sufficient portion of the membrane at the site where the specific binding pair member is located that a detectable signal can be identified if the substance of interest is present in the liquid. That is, in embodiments, the area where the specific binding pair member is bound to the porous membrane may exceed the area of direct contact with the porous material, but a sufficient amount of contact will be made such that the presence of the substance in the liquid can be detected.

Direct contact of the membrane and the material is preferred; however, one or more intervening porous, substantially hydrophilic materials may be interposed between the porous material and the porous membrane. In such a situation, the intervening porous materials effectively act as secondary porous materials, and thus can be considered for the purposes of the invention, to be a porous material or pad. Thus, use of the terms porous material or pad encompasses multiple materials that provide the same or essentially the same function.

In embodiments, contacting of the material and membrane comprises exerting pressure on the membrane and material to ensure complete or essentially complete contact of the two over at least a portion of the area where the specific binding pair member is located. While not necessary, it has been found that, under certain circumstances, pressure at this area may improve the performance of the method. For example, it can improve the sensitivity and reliability of the method. It can also improve the wicking characteristics of the porous material, which can increase the amount of sample in the reaction area. Pressure can further increase the amount of contact between the porous material and the porous membrane. That is, in embodiments where the porous material comprises both a sample application site and a reaction site, it has been found that compression of the porous material at the reaction site can improve the sensitivity of the device, and thus the assay or method of the invention. While not desiring to be limited to any particular theory of operation, it is believed that, in addition to improving the contact between the membrane and the material, compression of the reaction area of the porous material improves migration of liquid into the area of the material in contact with the membrane, and in particular the portion of the membrane comprising the specific binding pair member, and impedes migration of liquid out of the area. In effect, the compression causes the liquid to collect in the area of compression. The improved migration into, but not out of, the area causes an increase in the amount of substance in the area (as compared to an uncompressed material) and enhances diffusion of the substance (if present) into the porous membrane.

According to the method of the invention, the wetted porous material and the porous membrane are maintained in contact for a sufficient amount of time for the porous membrane to become wetted at least in a portion of the area comprising the specific binding pair member. Doing so permits the substance, if present in the sample, to diffuse through, over, around, and/or about the membrane and make contact with the specific binding pair member associated with the membrane. Although the amount of time provided will vary depending on the amount of substance in the sample, the porosity of the porous material and membrane, the amount of specific binding pair member associated with the membrane, the specificity and strength of binding of the specific binding pair member to the substance, the temperature, and other factors (all of which can be selected by those of skill in the art without undue experimentation based on times, concentrations, temperatures, etc. generally used in the art for rapid tests), typically, sufficient wetting of the membrane should occur within one minute. In preferred embodiments, the membrane and material are maintained in contact for at least thirty seconds, such as about or precisely thirty seconds, about or precisely one minute, about or precisely 2 minutes, about or precisely 3 minutes, about or precisely 5 minutes, about or precisely 10 minutes, about or precisely 15 minutes, about or precisely 20 minutes, about or precisely 25 minutes, or about or precisely 30 minutes. As used herein, unless otherwise noted, times, temperatures, and other numerical values recited include a range about the stated number of 5% at either end of the recited number. Thus, recitation of "60 seconds" includes any amount of time from 57 seconds to 63 seconds.

Maintaining the membrane and material in contact can be performed at any temperature. However, it is preferred that temperatures below 100° C. be used, such as room temperature (20°-25° C.), 30° C., 37° C., 40° C., or 50° C. Indeed, it has surprisingly been found that the present method can provide sensitivities greater than ELISA tests using the same specific binding pair member and substance, while being performed at room temperature rather than 37° C. (as is needed for an ELISA).

Likewise, any suitable concentration or amount of specific binding pair member and substance can be used. General amounts of various specific binding pair members (e.g., antibodies, enzymes, nucleic acids) to be used for membrane-bound detection of binding partners (e.g., antigens, enzyme substrates, nucleic acids or nucleic acid binding proteins) are known in the art. For example, when the specific binding pair member is an antibody, it can be present on the membrane at an amount of about 0.5 ng to about 1000 ug and over an area from about 0.5 square mm to about 100 square mm or more. Amounts to be bound to the membrane can be selected based on the amount of substance to be detected, the amount/intensity of signal intrinsically produced by the selected label and signal generation system, and the size of the area on which the specific binding pair member is bound. These parameters may be selected and adjusted by those of skill in the art based on well known characteristics of each signal generation system.

In embodiments, applying the liquid is performed before contacting the porous material with the porous membrane. In other embodiments, applying the liquid is performed after contacting the porous material with the porous membrane. Thus, in embodiments, the porous material and porous membrane are in contact with each other before the liquid is applied. In general, it is not important whether contact between the porous material and porous membrane occurs before or after application of the sample. The time at which contact is made is typically selected in conjunction with the configuration of the device used for a particular assay, and the ease of use of the device.

The method further comprises detecting the presence or absence of a complex comprising the specific binding pair member and the substance of interest, where the presence of such a complex indicates the presence of the substance in the liquid. According to the invention, if a sample contains a substance of interest, diffusion of the sample between the porous material (i.e., reaction pad) and porous membrane will permit the substance to come into contact with the specific binding pair member, which is bound to the membrane. The method of the invention detects the complex formed from the specific binding pair member and substance by any of a number of art-recognized detection schemes. For example, an antibody (other than the specific binding pair member bound to the membrane) that is specific for the substance can be exposed to the substance, either before the substance is exposed to the specific binding pair member (e.g., before the sample is applied to the porous material, while the sample is migrating through the porous material, etc.) or after sufficient time has been provided for the substance and specific binding pair member to come into contact. In some situations, the antibody will be labeled with a detectable moiety, such as with a label that can be directly detected (e.g., a metal sol, such as colloidal gold; a dye sol; a colored particle, such as latex); a paramagnetic bead; and a fluorescent compound. It can also be labeled with an indirect label, such as an enzyme that produces a detectable signal when exposed to a substrate (e.g., horseradish peroxidase, alkaline phosphatase). In other situations, the antibody will serve as a specific binding pair member for a label, such as by binding of the label to the Fc portion of the antibody. Labels can also include specific binding pairs in which one or both members contain a detectable moiety or substance that can generate a detectable moiety, such as an avidin (streptavidin)/biotin pair or any of its functional equivalents.

As alluded to in the previous paragraph, the label for the substance of interest may be provided as a component of the porous material. For example, it may be impregnated (as a dry substance or as a liquid solution that is permitted to dry in the porous material) in the reaction zone, the sample application zone, or the sample migration zone (located between the sample application zone and reaction zone in certain embodiments). As the liquid sample migrates into and through the porous material, the label is dissolved in the liquid and migrates along with the liquid to the reaction site and, eventually, to the membrane. During the migration process or during the reaction process, the label specifically binds the substance (if present), ultimately resulting in a membrane-bound complex comprising the specific binding pair member, the substance of interest, and the label. In embodiments where a label is included in the porous material, selection of the pore size of the material will depend, at least in part, on the migration characteristics of the label or the substance-label complex.

Detection of the substance can provide qualitative, semi-quantitative, or quantitative information on the substance in the sample. Qualitative detection provides information that informs the practitioner of the presence, but not necessarily the amount, of the substance in the sample. However, by placing a known amount of specific binding pair member on the membrane, by knowing the amount of substance that the specific binding pair member can bind, and by knowing the amount of substance-label complex that must be present for detection, one can provide a method of detection of a substance that is semi-quantitative. More specifically, by knowing these amounts, and by obtaining a detectable signal, the practitioner will know that the substance is not only present in the sample, but that the substance was present in at least an amount necessary to produce the detectable signal. If desired, quantitative measurement of sample amount can be obtained by comparing signal strength of the test sample with a standard curve of signal strengths derived from samples containing known amounts of substance. Various ways of designing semi-quantitative and quantitative assays are known in the art, and any suitable one may be used within this invention.

Detection may also be the absence of a detectable signal, or the diminution of a signal that would otherwise be generated in the absence of the substance or some other substance that is indicative of the presence of the substance. Thus, the methods of the invention encompass all types of immunoassays (including both sandwich-type assays and competitive assays) and any other assays that rely on detecting or failing to detect binding of at least one specific binding pair member to a substance of interest.

The method of the invention can comprise numerous other steps, including, but not limited to, providing one or more control reactions to determine whether one or more steps in the method have been performed successfully, to determine whether one or more reagents is functioning as expected, or to determine if substances that interfere with the ability of the method to generate reliable results are present in the sample. Substances that can be used as control reagents include, but are not limited to, the substance to be detected or a structural analog, an antibody that specifically reacts with another antibody, or anything else that can specifically bind to the substance of interest or some other reagent used in the assay. Accordingly, the method of the invention can include adding a known substance, including the substance to be detected, to determine if one or more steps of the method are working as designed. Such control reactions are well-known to those of skill in the art, and their design and implementation need not be detailed herein. A common control reaction will comprise providing a second area, either on the porous membrane that specifically binds the labeled substance or on a second porous membrane, to show not only that the label is present and functional, but to show that the label has had sufficient time to contact any binding partner associated with the membrane. Of course, multiple lines may be provided in various orientations, each providing repetitive or different information about various aspects of the method.

In addition, the method of the invention can detect one or more substances in the sample in addition to the substance of primary interest. The other substance(s) can be other substances that naturally occur in the sample being tested, or can be substances that are intentionally added to the sample to serve as positive controls, labels, competitors, and the like. Thus, the methods of the invention can detect two or more substances in a sample. When doing so, the multiple substances can be detected on the same porous membrane, or multiple membranes may be provided, either on the same device or on two identical devices (with the exception of the identity of the substance(s) bound to the membrane).

The method of the invention may comprise one or more washing steps. Although not limited to any particular method, washing is typically used in embodiments where indirect labels are used to detect the substance. For example, when using a label that uses a substrate to generate a signal (e.g., horseradish peroxidase), the label will typically be present in the reaction mixture in excess over the substance. In addition, it is possible that the substance-label complex might be present in excess over the specific binding pair member bound to the membrane. In either such situation, the excess label, if permitted to remain in and around the membrane comprising the specific binding pair member, would react with the label substrate to produce a signal, which would represent non-specific signal or background noise. To reduce this background noise, the membrane can be washed with an appropriate volume of an appropriate wash solution. The wash solution can be applied once or more than once, depending on the amount used and the amount of unbound label present. Likewise, other wash steps may be included at other points in the method. In embodiments, the wash step is used to wash unbound conjugate from the membrane to improve detection sensitivity. Those of skill in the art are well aware of advantages and disadvantages of performing or not performing washing steps at various points during specific binding reactions, and can thus select the type and number of washing steps, as well as the washing solutions, to use for each particular embodiment of the invention. Such selection can be made without undue experimentation.

In a second aspect, the invention provides a device for practicing the method of the invention. Broadly speaking, the device of the invention comprises any configuration of components that permit practice of the method of the invention. More specifically, the device of the invention comprises any number and configuration of components or elements that permit a liquid sample containing, or suspected of containing, a substance of interest to be retained in a pre-defined area or region of the device, where the area or region comprises a porous membrane comprising a specific binding pair member that is specific, either directly or indirectly, for the substance.

In its most basic form, the device of the invention comprises (a) a receptacle comprising a porous material that is capable of absorbing and transmitting a liquid, and (b) a porous membrane that comprises a specific binding pair member that is specific for a substance to be detected (be it the substance in the sample or a substance that binds to that substance), where the receptacle and porous membrane are each shaped to permit the porous membrane to be in direct contact with the porous material over at least a portion of the porous membrane that comprises the specific binding pair member. The device can further comprise a container containing the receptacle or a portion of the receptacle. The device can further comprise a holder for the porous membrane. In embodiments, the device comprises the container and holder in contact with each other, the contact between the two elements causing the porous membrane and the porous material to be in direct contact with each other over at least a portion of the porous membrane that comprises the specific binding pair member.

The receptacle is a physical and functional unit of the device. It provides an area and volume for liquids containing or suspected of containing a substance of interest to be retained. It also provides a reservoir for liquid to diffuse into and out of the porous membrane comprising the specific binding pair member, which is referred to herein as a reaction pad or zone. The receptacle can be of any shape and size, and fabricated of any suitable material. The receptacle comprises at least one porous material, also referred to herein as a pad. However, it is to be noted that the porous material is not necessarily limited in size to the area defined by the receptacle. That is, a single porous material or a combination of porous materials can be limited in size to the receptacle area or can extend beyond the receptacle area to the sample application area and/or wash area, or any other area present in a particular configuration of the device.

The porous material (also referred to herein as a "pad") can be fabricated from any material that has pores, holes, or spaces through which one or more liquids can pass. It is thus any material that is absorbent. Non-limiting examples of porous materials include, but are not limited to, paper products, such as bibulous or filtration paper (e.g., Whatman® 3 mm paper, and Filtrona® products), synthetic polymeric materials (e.g., nitrocellulose, nylon), plastics and plastic spheres (e.g., Porex® plastic beads; materials used in fabricating ballpoint pens), such as those made from polypropylene, polyethylene, polyvinylidene fluoride, ethylene vinylacetate, acrylonitrile, and polytetrafluoroethylene. Other non-limiting examples include nanoparticles/spheres/tubes.

The pore size of the material can be selected based on the characteristics desired. Numerous porosities are available for the various types of materials that the porous material can be made from. For example, if a sample to be applied contains particulate materials or solids (e.g., feces, soil), a pores size that excludes or significantly slows the migration of these particulate materials or solids can be chosen. Likewise, if the sample comprises blood, a pore size that excludes or significantly slows the migration of blood cells and platelets can be chosen. Alternatively, if the sample does not contain any substances that are undesirable at the detection site (e.g., a sample that has been pre-purified to some extent), the pore size of the material may be selected without regard to filtration characteristics. In general, the pore size will range from about 0.05 micrometers to about 0.5 micrometers.

The porous material may be fabricated from a single material or may comprise multiple different porous materials. The differing individual materials may be configured in any suitable configuration, such as layering one on top of another, abutting of two materials end-to-end, or any other configuration that permits a liquid to flow from one area of the material to another, such as from the site of application of a liquid to the site of detection on the porous membrane, when in contact with the porous material. For example, the porous material may comprise a pore size and material of one type at the site of application of the liquid (the application zone), a second pore size and/or material at the site of detection (the detection zone), and a third pore size and/or material (which can be the same as the first) at a third area distal (with respect to the site of application of the liquid) to the detection site, the third site functioning as a wash solution receiving site (the wash receiving zone). The pore sizes and materials, and combinations thereof, may be selected to suit individual needs based on the various characteristics of the sample, the substance to be detected, the configuration of the device, or any other consideration. The porous material may contain substances that are deemed useful in practicing the invention, including, but not limited to, labels for the substance, activated charcoal, ion exchange resins, and surface active agents. Furthermore, the porous materials can be separated from each other by less porous, non-porous, or impermeable materials, such as hydrophobic membranes. These membranes can be removed at some point during practice of a method of the invention to permit flow of liquids from one or more materials to one or more other materials. For example, the two porous materials may be separated by a non-porous material attached to a pull-tab. Pulling of the tab removes the non-porous material and permits flow of liquids, such as wash solution, into a porous material (e.g., a wash pad).

The porous membrane is a membrane made of any suitable material that permits liquids and suspended substances of a pre-determined size to flow through it. Typically, the membrane is fabricated from materials known in the art to be suitable for detection of substances of interest by specific binding of a membrane-bound molecule to a substance. Examples include, nylon membranes, nitrocellulose membranes, polyvinylpyrolidone membranes, glass fibers, and the like.

The porous membrane comprises at least one specific binding pair member. The specific binding pair member is associated with the membrane in such a way that it remains associated with the membrane under the conditions of fabrication and use of the device. Typically, the specific binding pair member is bound, by covalent, ionic, or hydrophobic bonds, to the membrane. The membrane may be treated prior to binding in order to enhance binding. Likewise, the membrane may be treated after binding to enhance binding or to reduce binding of other substances to sites on the membrane that are different than the site where the specific binding pair member is bound. The specific binding pair member may be bound to the membrane using any known technique. Furthermore, it may be bound to the membrane in any shape, design, pattern, direction, etc. desired (e.g., a line, a cross, a dot, a circle) and in any size desired (e.g., a dot of diameter of 0.1 mm, 1 mm, 2 mm, 3 mm, 4 mm, 5 mm, etc.; a line 1 mm thick and 5 mm long, 2 mm thick and 1 cm long, etc.). In preferred embodiments, it is in the shape of a line, which provides an advantageous and convenient detection shape. In embodiments, the porous membrane comprises two or more different areas containing a specific binding pair member. In certain embodiments, two or more areas comprise the same specific binding pair member. In other embodiments, each area comprises a different specific binding pair member. The different specific binding pair members may be specific for the same substance (to provide an internal reproducibility control), or may be specific for different substances (e.g., one is specific for a substance of interest, while one or more others are specific for other substances of interest or for reagents used in the method of the invention).

Thus, the porous membrane may comprise other components in addition to the specific binding pair member. For example, it may comprise a molecule to be used as a control for the performance of the method of the invention, such as an antibody that specifically binds the label used to detect the substance of interest in the sample. It may also comprise a second specific binding pair member, the second specific binding pair member being specific for a second substance of interest in the sample (including a substance that is intentionally added to the sample to serve as a positive control). As discussed above, the specific binding pair member may be an antigen or antibody in a binding pair, a receptor or ligand in a binding pair, or either component of a binding pair. Thus, the present invention contemplates binding an antibody, an antigen, a receptor, a ligand, a single stranded nucleic acid, etc. to the membrane in order to detect its binding partner.

In embodiments, the porous membrane is in contact with a holder. The holder can hold the membrane in place such that the membrane stays in contact, over at least a portion of the membrane, with the reaction pad. It also can hold the membrane in a position such that it is capable of being placed in contact with the reaction pad if so desired. For example, the holder can be a plastic ring, square, etc. that contacts the membrane. Contact can either retain the membrane on the holder or simply retain the membrane in contact with the reaction pad. The holder may be a separate physical component of the device or it may be fabricated as an integral portion of the device, for example as an integral portion of the container of the device.

The receptacle may be located within a container. The container may be fabricated of any suitable material, but is typically made of plastic. The container provides substantial structural strength and liquid impermeability to the device of the invention, and may provide other functions as well. In a basic configuration of the device of the invention, the container contains the reaction pad, and comprises the membrane. The membrane can be provided in any suitable fashion that permits contact of the membrane with the reaction pad.

For example, the membrane may be bound to a holder that is connected to the container through a hinge. Alternatively, the membrane may be bound to a holder that is integral with the container, where the container is fabricated from two halves that fit together such that the membrane contacts the reaction pad. Other suitable configurations will be apparent to those of skill in the art, and all such configurations are encompassed by the invention.

The device of the invention can further comprise a sample application area or zone (also referred to herein as the sample application pad) comprising a porous material. As described above, the sample may be applied to the receptacle or reaction pad. However, in embodiments, the sample is added at a site distant to the receptacle and reaction pad. In such embodiments, the sample is added at the sample application pad, which comprises a porous material. The porous material of the sample application pad may be the same material as that used in the reaction pad (i.e., it may physically be the same element or it may be two separate elements fabricated from the same material). Alternatively, it may be a different material, where the two materials are placed in contact with each other so that liquid from the application pad may pass into the reaction pad.

The size of the sample application zone is not critical. However, it is preferred that the sample application zone and the reaction zone, together, have sufficient absorbent ability to absorb the entire sample being applied. Furthermore, the sample application zone may comprise an open area not containing the application pad, the area typically being defined by the edge of the application pad and the side of the container. This open area may be designed to accept, either directly or as overflow, the sample being added, and may function to help filter and retain solids and large particles present in the sample.

The device may further comprise a wash solution receiving zone or area (also referred to herein as a wash solution receiving pad) comprising a porous material. The porous material of the wash solution receiving pad may be the same material as that used in the reaction pad and/or sample application pad (i.e., it may physically be the same element as the reaction and sample application pads, or it may be a separate element fabricated from the same material as one or both of the other pads). Alternatively, it may be a material that is different than either or both of the reaction pad and the sample application pad. In such a situation, the wash solution receiving pad is placed in contact with the reaction pad, the application pad, or both, so that wash liquid from the membrane (flowing through the reaction pad) may pass into the wash liquid pad.

In embodiments, a removable liquid impermeable or semi-permeable barrier is interposed between the wash solution receiving pad and one or more other pads of the device. The barrier is present in embodiments to ensure that no liquid from the reaction pad or application pad enters into the wash solution receiving pad until the wash solution is added to the device. While typically not necessary due to the liquid flow and retention characteristics of the reaction pad, the barrier may be included in the device for added assurance, to increase the amount of liquid present in the reaction pad, or for any other reason. In other embodiments, one or more liquid impermeable barriers are included between one or more of the various pads present in the device.

The device may comprise a filtration pad or zone between the sample application pad or zone and the reaction pad or zone. While the sample application pad and reaction pad can provide suitable filtration of the sample, it may sometimes be desired to have additional filtration of the sample prior to exposure of the sample to the membrane. In such situations, a filtration pad may be provided. In embodiments, the filtration pad is simply an extension of the reaction pad beyond the area covered by the membrane. Alternatively, it can simply be an extension of the sample application pad that extends beyond the area where the sample is applied. In some embodiments, the sample application pad, filtration pad, and reaction pad are the same element, the various "pads" being designated (or referred to as "zones") based on function and location within the device rather than on physical characteristics. The primary function of the filtration pad is to block or retard migration of certain substances to the reaction pad. Such filtration may benefit the detection of the substance of interest by retarding colored compounds, retarding large particles that would cause background noise, and the like.

As can be seen from the above description, the reaction pad, sample application pad, and filtration pad all may be fabricated from a porous material (either the same material or different materials). Likewise, the wash solution receiving pad may be fabricated from a porous material. The porous materials serve various functions, but generally all serve to draw liquid through the material such that it passes to another material. For example, the sample application, filtration, and reaction pads permit liquid to travel from the site of application to the site of detection (i.e., the membrane), while simultaneously filtering various solids and particles, colored materials, or other substances. The wash solution receiving pad can draw liquid from the reaction pad when wash solution is added to the membrane, thus permitting the wash solution to carry away unwanted substances that might interfere with specific detection of the substance on the membrane.

The porous material serves various functions within each area or zone, and these functions significantly overlap with the functions that can be provided in other areas of the device that comprise a porous material. For ease of description, many of the functions have been described with respect to each particular area of the device; however, the characteristics should not be considered to be limited to only the areas for which the characteristic has been described. The particular physical location of the porous material in differing embodiments will be apparent to those of skill in the art, and the particular functions of the porous material in each area will likewise be apparent. The characteristics should not be considered limiting to that area. For example, in the receptacle region, the primary functions of the porous material are to provide an area or volume for liquids containing or suspected of containing a substance of interest to be retained, to provide a reservoir for liquid to diffuse into and out of the porous membrane comprising the specific binding pair member, and to draw liquid into the reaction area. Thus, the porous material in this region is sometimes referred to herein as the "reaction pad". However, in certain embodiments, the reaction pad is also the sample receiving area, and thus also functions to receive, and typically filter, the sample as well. Furthermore, due to placement of the membrane in contact with the reaction pad, the reaction pad serves as the initial acceptor for wash solution in embodiments where the membrane is washed. Accordingly, the reaction pad serves as an initial wash solution receiving pad as well.

Of course, other elements can be included in the device of the invention to provide various advantages. All such additional elements are to be understood as encompassed by the present invention. Furthermore, additional method steps that provide additional advantages can be included, and are encompassed by the invention. Those of skill in the art are capable of including such elements and methods steps without undue experimentation and without departing from the full scope and spirit of the invention.

In embodiments, the device is provided in a kit. The kit can comprise the device alone, in one or more copies of the same or multiple different various configurations. Alternatively, the kit may comprises other materials, such as some or all of the materials, reagents, and equipment needed to practice at least one embodiment of the method of the invention.

The kits themselves can be fabricated from any suitable material, such as cardboard, plastic, metal, or glass. Cardboard and plastic are preferred materials for the kits. The kits are fabricated to suitably contain all of the components provided by the kit. Thus, they are designed to be the appropriate size, shape, and strength for holding the various components selected to be provided by the kit.

The components provided by the kits can be in one or more containers. Containers of the device of the invention are described above, and can be made of any suitable material, including any of the various plastic materials known to be useful in fabricating devices of this nature. Containers for other components can be made of any suitable material, including, but not limited to, plastic (e.g., a polymeric material), glass, metal, and rubber. The containers can be in any shape or form, and thus can be, for example, bottles, vials, cans, jars, or bags, such as those made of metal, plastic, rubber, glass, or fabric. The containers are preferably re-sealable or automatically sealing to preserve unused contents after initial opening.

Thus, in embodiments, the kits comprise one or more devices (e.g., 10, 20, 25, 30, 50, 100) and at least one container containing a component that is useful for practicing at least one embodiment of the invention. For example, a kit can comprise 25 devices, sealed independently or two or more together, in re-sealable pouches. Optionally, the pouches can contain a dessicant to maintain low moisture content during storage. The kit may also comprise any one or more of the following components, in any suitable container(s) and amounts/volumes: diluent (preferably aqueous) for diluting an original sample; wash buffer (preferably aqueous); specific binding pair member (e.g., a conjugate for binding to the substance of interest in the sample, and which can be bound by an antibody spotted on the porous membrane of the device); substrate (e.g., a substrate for an enzymatic reaction or otherwise for producing a detectable signal); positive control (e.g., an antigen of known identity that binds with a known affinity to an antibody that is spotted on a porous membrane of the device); pipette (e.g., disposable pipettes for adding one or more reagent, etc. to the sample or device); test tube, gloves, applicator stick, pipette tips. Other optional components of the kits can be envisioned by those of skill in the art, and all such other components are encompassed by the present invention.

Preferably, at least the devices are sterilized prior to, during, or after insertion into the kits. Preferably, one, some, or all of the other components are sterilized prior to, during, or after insertion into the kit. In highly preferred embodiments, each component in the kit is sterile or has been sterilized, either independently of one or more of the other components, or together in the kit. Sterilization can be achieved by any known means, including, but not limited to, filtration of liquids, irradiation by electromagnetic radiation (e.g., UV, gamma irradiation), chemical sterilization (e.g., wiping with a disinfectant such as alcohol), and the like.

Instructions for using one or more components of the kit, or for practicing the methods of the invention, may be included in the kit. The instructions may be provided as a separate component, such as printed material on a paper, card, plastic sheet, or the like. Alternatively, the instructions may be provided on the kit itself, for example, on a side or the top or bottom of the kit. Alternatively, the instructions may be provided on a container for a component of the kit.

Turning now to the Figures, which depict various non-limiting specific embodiments of the invention, the elements described above are described in various spatial relationships to each other, and use of various configurations of the device of the invention to perform the method of the invention is described. It is to be understood that any dimensions provided in the Figures are provided as examples only, and that the actual sizes and shapes of the device are not limited to those provided in the Figures. For example, sizes can be on the order of a magnitude or more larger or smaller than those exemplified in the Figures. Furthermore, it is to be understood that the Figures do not necessarily depict all elements at proper scale with respect to each other, some being exaggerated for clarity purposes or for other reasons.

FIG. 1 depicts generally a basic configuration of the device 1 of the present invention. The device depicted in FIG. 1 comprises a receptacle 100 that comprises a porous material in the form of a pad 110 (also referred to herein as the "reaction chamber pad"). The device further comprises a porous membrane 120 that comprises a specific binding pair member 130 for a substance of interest that is attached, by covalent, hydrophobic, or ionic bonding, along a single line in the center of the membrane. In practicing the invention with this configuration of the device, a liquid sample containing or suspected of containing a substance of interest is applied to the receptacle 100 at any area. The porous membrane 120 is then placed in direct contact with the porous material 110 of the receptacle 100 such that the membrane 120 and material 110 form a continuous contacting surface over at least the area of the membrane 110 where the specific binding pair member 130 is located. The liquid present in the porous material 110 is then permitted to diffuse into, out of, through, and around the membrane 120, enabling the substance, if present, to contact the specific binding pair member 130 and become specifically bound to it. In embodiments where the substance has already been labeled, detection of binding can be accomplished at this point. In embodiments where a label has not yet been associated with the substance, the specific binding pair member-substance complex can be labeled and then detected. In embodiments, a wash step is included to reduce background. When a wash is performed, the wash solution is applied to the membrane 120 and permitted to soak into the porous material 110, thus removing materials that are not bound to membrane 120, and improving the signal-to-noise ratio. In embodiments, the substance in the sample is first bound by a specific binding member that specifically binds to the one associated with the membrane (e.g., a conjugate), and the two specific binding pair members are allowed time to react.

The device 1 of FIG. 1 is also referred to at various points below as a "reaction chamber" when used in conjunction with other elements.

Figure 2:
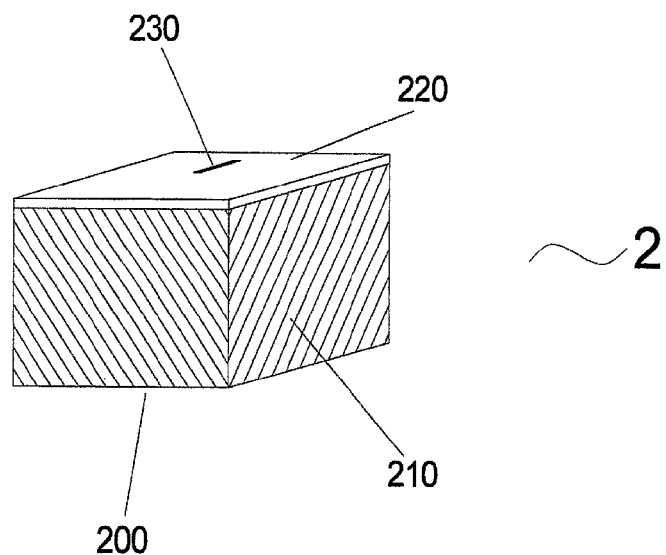
FIG. 2 is a perspective view of a configuration of the device depicted in FIG. 1, in which the porous membrane is in direct contact with the porous material.

With respect to FIG. 2, a device 2 of the invention is depicted that comprises a receptacle 200 comprising a porous material 210. In this embodiment, the porous membrane 220 is in contact with the porous material 210 such that there is continuous contact between porous membrane 220 and porous material 210 in the area of specific binding pair member 230. In practice of the method of the invention with this configuration of the device, a liquid sample containing or suspected of containing a substance of interest is applied to the receptacle at any area other than the area in contact with porous membrane 220. The liquid present in the porous material is then permitted to diffuse into, out of, through, and around membrane 220, enabling the substance, if present, to contact specific binding pair member 230 and become specifically bound to it. In embodiments where the substance has already been labeled, detection of binding can be accomplished at this point. In embodiments where a label has not yet been associated with the substance, the specific binding pair member-substance complex can be labeled and then detected. In embodiments, a wash step is included to reduce background. When a wash is performed, the wash solution is applied to membrane 220 and permitted to soak into porous material 210, thus removing materials that are not bound to membrane 220, and improving the signal-to-noise ratio.

Figure 3:
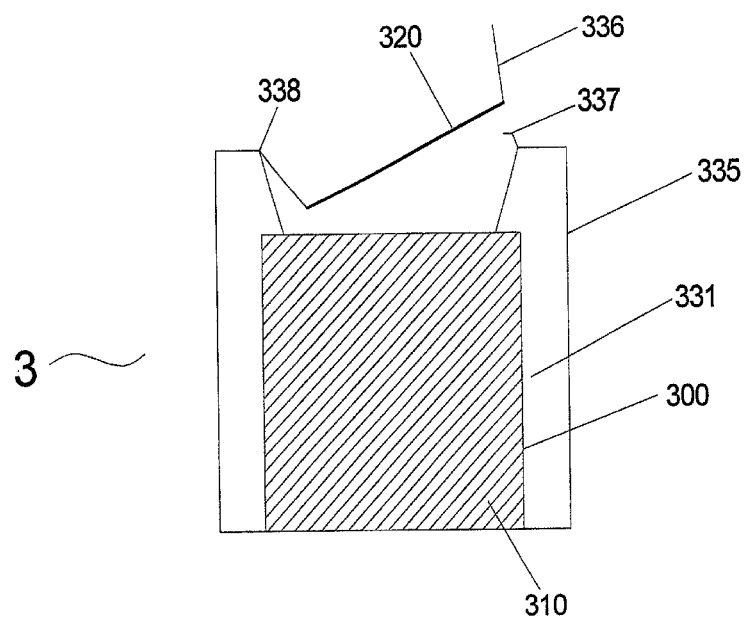
FIG. 3 is a cross-section side view of a configuration of a device of the invention, comprising a container and holder directly connected to each other by way of a flexible hinge.

FIG. 3 depicts another embodiment of the device 3 of the invention, in which receptacle 300 comprising porous material 310 is contained in container 335, and wherein porous membrane 320 is held by holder 336. In this embodiment, holder 336 and container 335 are fabricated from plastic. Holder 336 is integral with container 335, the two linked by a relatively flexible portion of the plastic at hinge 338. In other embodiments, other materials and/or other structures are used, including, but not limited to use in providing the hinge function.

In practicing the method of the invention with this configuration of the device of the invention, a liquid sample containing or suspected of containing a substance of interest is applied to the receptacle 300 at any area of the porous material 310, either directly or by way of the space present between the receptacle 300 and the container 335, such as in area 331. Holder 336 comprising membrane 320 is then swung down by way of hinge 338 such that membrane 320 is in contact with porous material 310, at least at a portion of membrane 320 where specific binding pair member (not depicted) is present. Clamp or lip 337 engages holder 336 to maintain membrane 320 in contact with material 310, as described above. The liquid present in porous material 310 is then permitted to diffuse into and out of membrane 320, enabling the substance, if present, to contact specific binding pair member (not depicted) present on membrane 320 and become specifically bound to it. In embodiments where the substance has already been labeled, detection of binding can be accomplished at this point. In embodiments where a label has not yet been associated with the substance, the specific binding pair member-substance complex can be labeled and then detected. In embodiments, a wash step is included to reduce background. When a wash is performed, the wash solution is applied to membrane 320 and permitted to soak into porous material 310, thus removing materials that are not bound to membrane 320, and improving the signal-to-noise ratio.

Figure 4A:
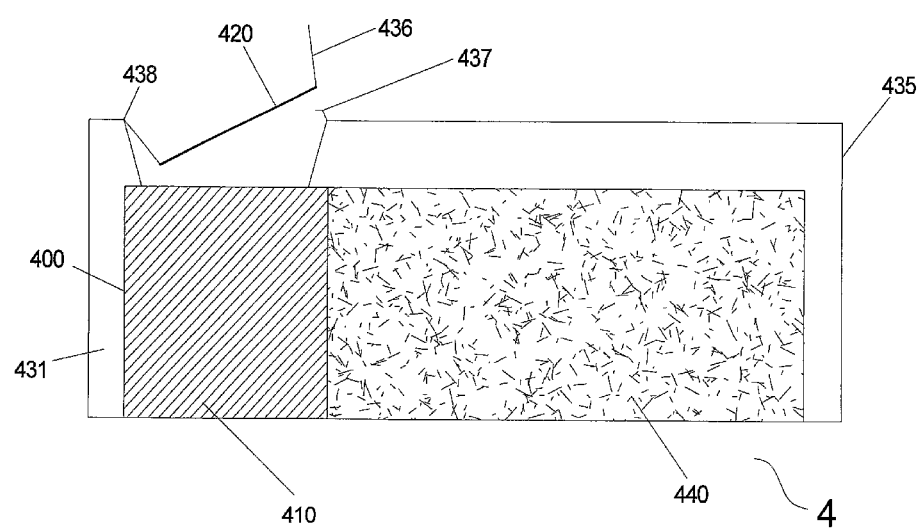
FIG. 4A is a cross-section side view of a configuration of a device of the invention in which a wash solution receiving pad is connected to a sample receiving and reaction pad.

FIG. 4A depicts a device 4 of the invention in which the device 3 of FIG. 3 is modified to include a wash solution receiving pad 440 positioned in contact with porous material 410. Wash solution receiving pad 440 is fabricated from a porous material which can be the same or different from reaction pad 410. In this embodiment, wash solution receiving pad 440 is a separate pad from reaction pad 410; however, in other embodiments, reaction pad 410 and wash receiving pad 440 are the same element, the differentiation being based primarily on function.

More specifically, receptacle 400 comprising reaction pad 410 is contained in container 435, which contains not only receptacle 400 but wash receiving pad 440 as well. Porous membrane 420 is held by holder 436. In this embodiment, holder 436 and container 435 are fabricated from plastic and holder 436 is integral with container 435, the two linked by a relatively flexible portion of the plastic at hinge 438. In other embodiments, other materials and/or structures are used, such as to provide the hinge function.

In practicing the method of the invention with this configuration of the device of the invention, a liquid sample containing or suspected of containing a substance of interest is applied to the receptacle 400 at any area of reaction pad 410, either directly or by way of the space present between the receptacle 400 and the container 435, such as in area 431. Holder 436 comprising membrane 420 is then swung down by way of hinge 438 such that membrane 420 is in contact with reaction pad 410, at least at a portion of membrane 420 where specific binding pair member (not depicted) is present. Clamp or lip 437 engages holder 436 to maintain membrane 420 in contact with reaction pad 410, as described above. The liquid present in reaction pad 410 is then permitted to diffuse into and out of membrane 420, enabling the substance, if present, to contact specific binding pair member (not depicted) present on membrane 420 and become specifically bound to it. In embodiments where the substance has already been labeled, detection of binding can be accomplished at this point. In embodiments where a label has not yet been associated with the substance, the specific binding pair member-substance complex can be labeled and then detected.

In embodiments, a wash step is included to reduce background. When a wash is performed, the wash solution is applied to membrane 420 and permitted to soak into reaction pad 410, thus removing materials that are not bound to membrane 420, and improving the signal-to-noise ratio. Typically, the amount of wash solution applied to membrane 420 exceeds the holding capacity of pad 410, which has already been wetted (at least partially) with the liquid containing the substance of interest. In this situation, excess wash solution (and some original liquid sample) travels through reaction pad 410 into wash solution receiving pad 440.

Figure 4B:
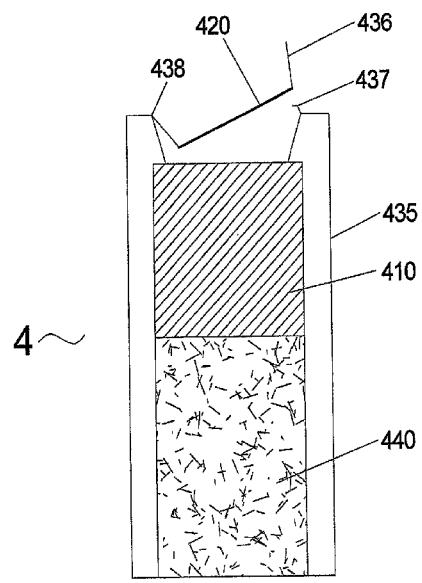
FIG. 4B is a cross-section side view of an alternative configuration of the device depicted in FIG. 4A, in which the wash solution receiving pad is located below the sample receiving and reaction pad.

FIG. 4B depicts an alternative configuration of the device 4 of the invention depicted in FIG. 4A, in which wash solution receiving pad 440 is located beneath reaction pad 410. The principle of operation of the device is the same as described with respect to FIG. 4A. However, in this configuration, it is not preferred that the liquid be applied in the space between reaction pad 410 and container 435. In this Figure, all elements have the same identity as those in FIG. 4A.

Figure 4C:
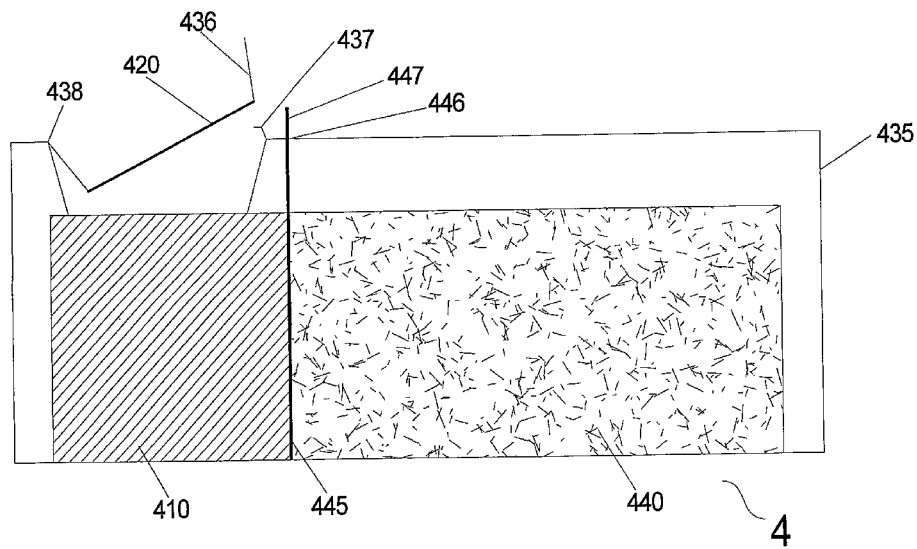
FIG. 4C is a cross-section side view of a configuration of the device of the invention in which a removable liquid impermeable barrier is located between a sample receiving and reaction pad and a wash solution receiving pad.

FIG. 4C depicts an alternative configuration of the device depicted in FIG. 4A, in which wash solution receiving pad 440 and reaction pad 410 are separated by removable, liquid-impermeable barrier 445. In this configuration, impermeable barrier 445 is interposed between wash solution receiving pad 440 and reaction pad 410 and extends to the exterior of container 435 through slot 446 to expose tab 447. Practice of the method of the invention with this configuration is similar to that described above with respect to FIG. 4A. However, because impermeable barrier 445 blocks migration of liquids into wash solution receiving pad 440, impermeable barrier 445 is typically removed after contacting of membrane 420 and reaction pad 410 and before application of wash solution to membrane 420. Use in this manner also restricts flow of the original sample from application/reaction pad 410 into wash receiving pad 440 until after diffusion of the sample in and out of membrane 420 has proceeding for a desired amount of time. All other elements depicted in this panel are the same as those described with regard to FIG. 4A.

Figure 5:
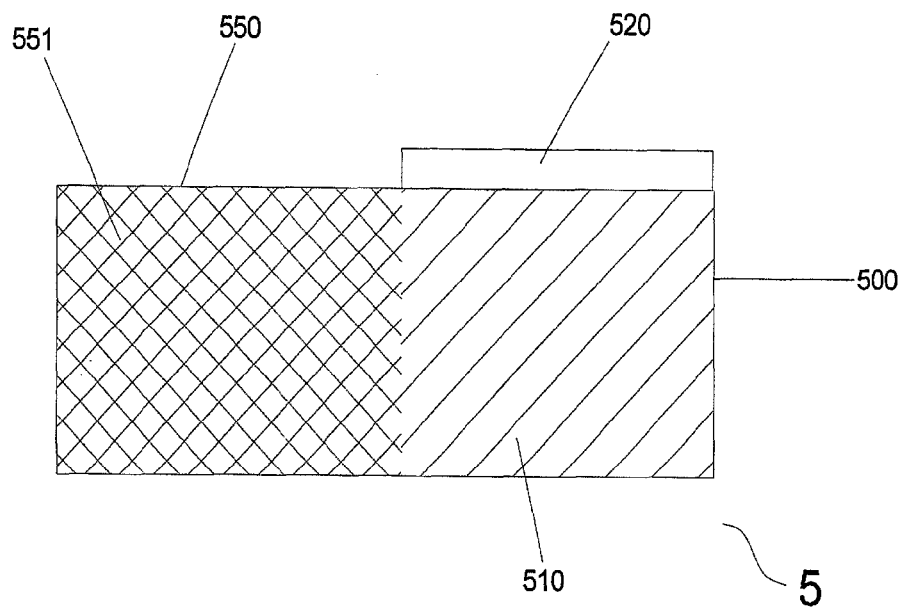
FIG. 5 depicts a side view of a configuration of the device of the invention in which the sample receiving and reaction pad is extended beyond the reaction area, to form a unit comprising a separate sample receiving area and a reaction area.

In another configuration of the device, depicted in FIG. 5, the basic design depicted in FIG. 1 is modified to produce a device 5 such that the porous material 510 of the receptacle 500 extends beyond the reaction chamber (i.e., is larger than the area of the porous membrane 520) to provide a liquid sample application zone 550 comprising a sample application pad 551. In the depicted embodiment, the sample application pad 551 and the reaction pad 510 are the same. However, in other embodiments, these two elements are separate, and are arranged such that they are in physical contact with each other so that liquid may flow from one to the other. In practicing the invention with this configuration of the device, a liquid sample containing or suspected of containing a substance of interest is applied to the sample application pad 551 at any area within sample application zone 550. Due to its porous nature, sample application pad 551 causes at least a portion of the applied sample to migrate to reaction pad 510, where it can then migrate, through passive diffusion, into and out of porous membrane 520, and allow the substance of interest, if present, to contact and bind to specific binding pair member (not depicted) on porous membrane 520. Detection and washing, if desired, can be performed as described above.

Figure 6:
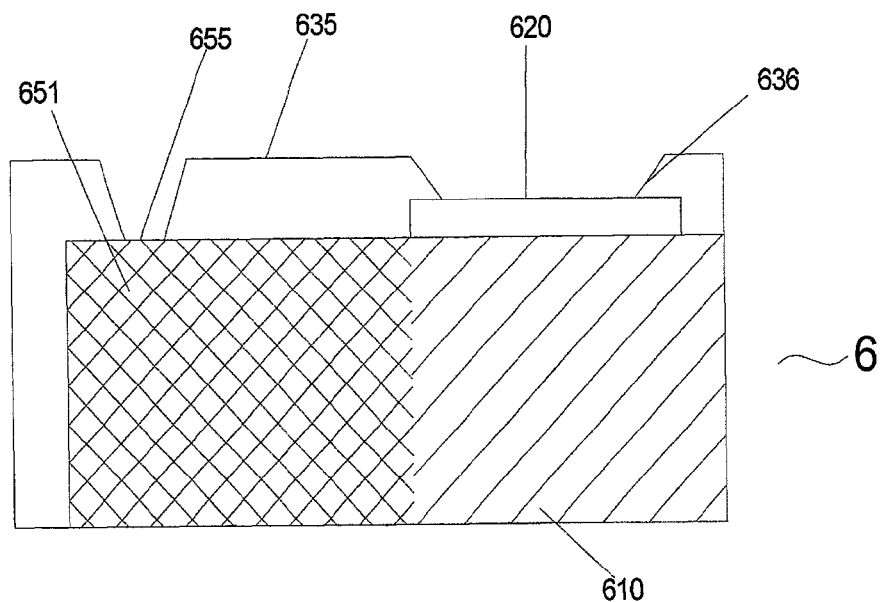
FIG. 6 depicts a cross-section side view of the device depicted in FIG. 5 contained within a container that comprises a sample application port and a viewing window.

FIG. 6 depicts device 6, which is a configuration of the device of the invention as depicted in FIG. 5, but modified to include a container 635 for the sample application pad 651 and reaction pad 610, and to include a holder 636 for porous membrane 620. In this particular embodiment, container 635 comprises an opening or port 655 that permits application of the liquid sample to application pad 651. Use of this embodiment of the device can proceed as discussed above.

Figure 7:
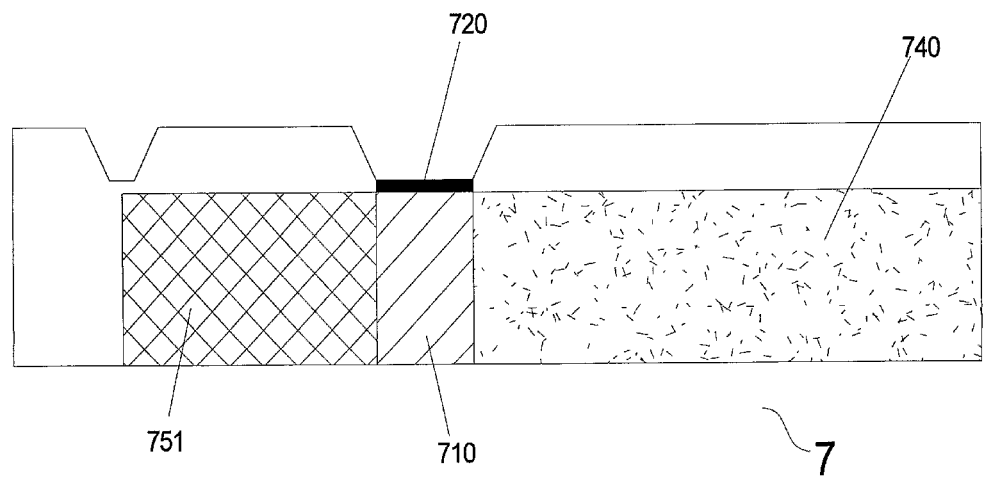
FIG. 7 depicts a cross-section side view of a configuration of the device of the invention comprising a sample application port and a viewing window.

FIG. 7 depicts device 7, which is a configuration of the device depicted in FIG. 6 in which a wash solution receiving pad 740 is provided adjacent to and in contact with reaction pad 710. In practice of the invention with this configuration of the device, after sample application to sample application pad 751, migration of the liquid to reaction pad 710 and diffusion of the liquid into and out of porous membrane 720, a wash solution is added to membrane 720 and the excess wash solution (along with a portion of the original liquid sample) flows through reaction pad 710 into wash solution receiving pad 740. All elements depicted in this Figure other than those specifically referenced are the same as those in FIG. 6 and/or FIG. 5, where like elements depicted are the same element from figure to figure.

Figure 8:
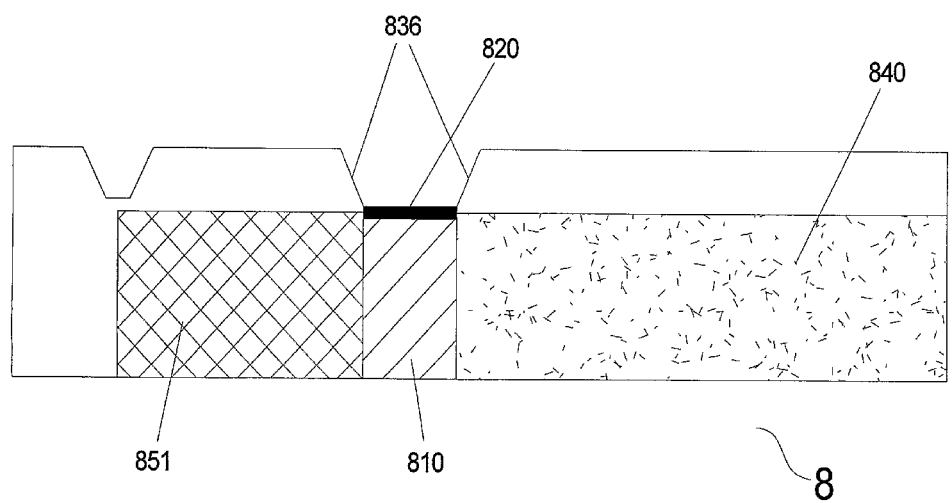
FIG. 8 depicts a cross-section side view of a configuration of the device of the invention in which the holder for the porous membrane exerts pressure on the reaction pad at the site of the membrane to cause compression of the pad at this area.

FIG. 8 depicts device 8, which is a configuration of the device of the invention in which reaction pad 810 is fabricated from the same material as liquid sample application pad 851 and wash solution receiving pad 840, but is compressed, as compared to sample application pad 851 and wash solution receiving pad 840, by pressure exerted by holder 836. In this preferred embodiment of the invention, pressure is exerted on membrane 820, which causes compression of reaction pad 810. This compression improves retention of sample in reaction pad 810, and promotes diffusion of sample between reaction pad 810 and membrane 820. All elements depicted in this Figure other than those specifically referenced are the same as those in FIG. 7, FIG. 6, and/or FIG. 5, where like elements depicted are the same element from figure to figure.

Figure 9:
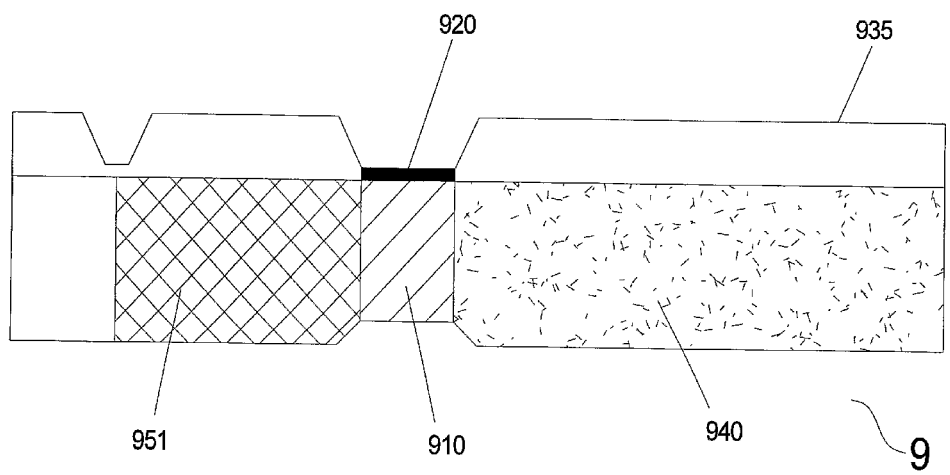
FIG. 9 depicts a cross-section side view of a configuration of the device of the invention in which the container exerts pressure on the reaction pad from underneath at the site of the membrane to cause compression of the pad at this area.

FIG. 9 depicts device 9, which is a configuration of the device of the invention in which reaction pad 910 is fabricated from the same material as liquid sample application pad 951 and wash solution receiving pad 940, but is compressed, as compared to sample application pad 951 and wash solution receiving pad 940, by pressure exerted from below (with respect to porous membrane 920) by container 935. In the Figure, compression results from container 935, which is molded into a shape that provides this effect. However, in other equivalent embodiments, container 935 comprises an additional element that provides the pressure on reaction pad 910. Exertion of pressure by container 935 provides the same benefits described above with respect to FIG. 8 and as discussed other places in the description. All elements depicted in this Figure other than those specifically referenced are the same as those in FIG. 8, FIG. 7, FIG. 6, and/or FIG. 5, where like elements are depicted and/or numbered the same from figure to figure.

Figure 10:
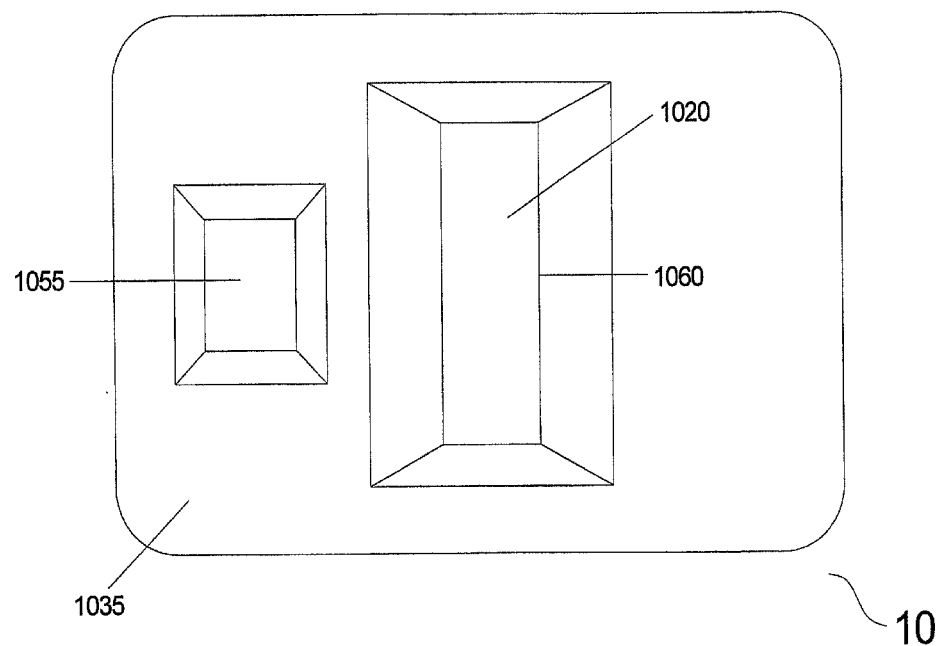
FIG. 10 depicts a top view of a configuration of the device of the invention, showing a sample application port and viewing window.

FIG. 10 shows a configuration of device 10 of the invention, looking at the outside of device 10 from the top. In this Figure, sample application port 1055 is located at one end of device 10, and an opening in device 10 above porous membrane 1020 provides a detection window 1060 through which detection of the presence of the substance of interest (and, optionally, one or more control reactions) can be viewed. Port 1055 and window 1060 are located on container 1035. In practicing the method using this embodiment of the device, sample is added to an application pad or reaction pad below or near port 1055, either directly to the pad or to a space between the pad and container 1035. The sample, or a portion of it, travels along the pad at least until it comes into contact with membrane 1020, preferably through a reaction pad (not depicted) beneath membrane 1020. Diffusion of the sample in, out, across, and over membrane 1020 permits contact between the substance of interest in the sample and a specific binding pair member (not depicted) associated with membrane 1020. Detection of the substance bound to the specific binding pair member on the membrane can occur by viewing the membrane through window 1060.

Figure 11:
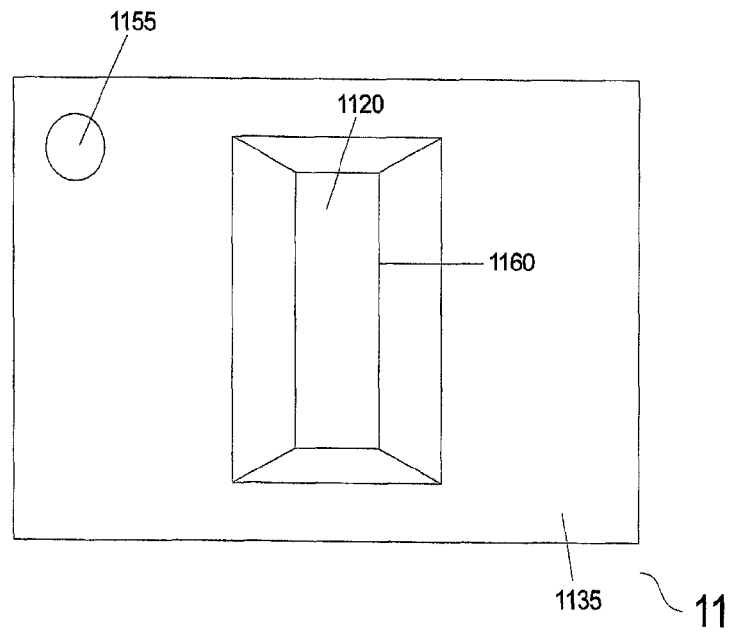
FIG. 11 depicts a top view of an alternative configuration of the device of the invention, showing a sample application port and viewing window.

FIG. 11 shows an alternative configuration of the device 11 depicted in FIG. 10. In this configuration, sample application port 1155 is located at one corner of device 11, and detection window 1160 and membrane 1120 are centrally located. In practice of the method of the invention with this embodiment of the device, sample is added to an application pad or reaction pad (not depicted) beneath or near port 1155, either directly to the pad or to a space between the pad and container 1135. The sample, or a portion of it, travels along the pad at least until it comes into contact with membrane 1120. Diffusion of the sample in, out, across, and over membrane 1120 permits contact between the substance of interest in the sample and a specific binding pair member associated with membrane 1120. Detection of the substance bound to the specific binding pair member on the membrane can occur by viewing the membrane through window 1160.

Figure 12:
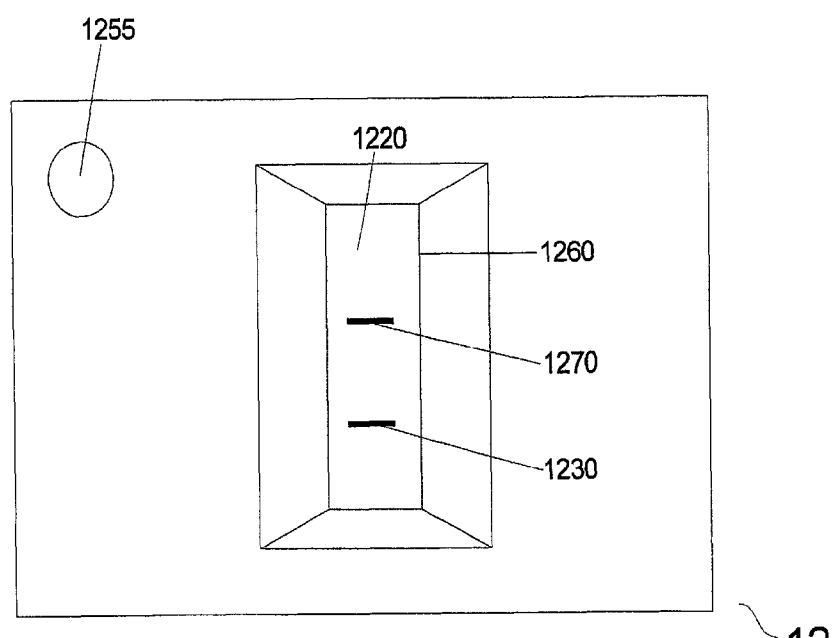
FIG. 12 depicts a top view of the device depicted in FIG. 11, with areas comprising specific binding pair members and/or control molecules on the membrane within the area defined by the viewing window.

FIG. 12 shows a top view of a configuration of device 12 of the invention in which porous membrane 1220 comprises specific binding pair member 1230, which is specific for the substance of interest, and positive control 1270. In this configuration, both elements are located on membrane 1220 such that they are within the area defined by detection window 1260. All of the elements depicted in FIG. 12 that are not specifically discussed are the same as those depicted in FIG. 11, and all have the same function. Practice of the method of the invention proceeds according to the disclosure above. Practice of the method using this embodiment of the device permits a single sample to be tested for an unknown substance while providing a positive control for performance of the device and method.

Figure 13:
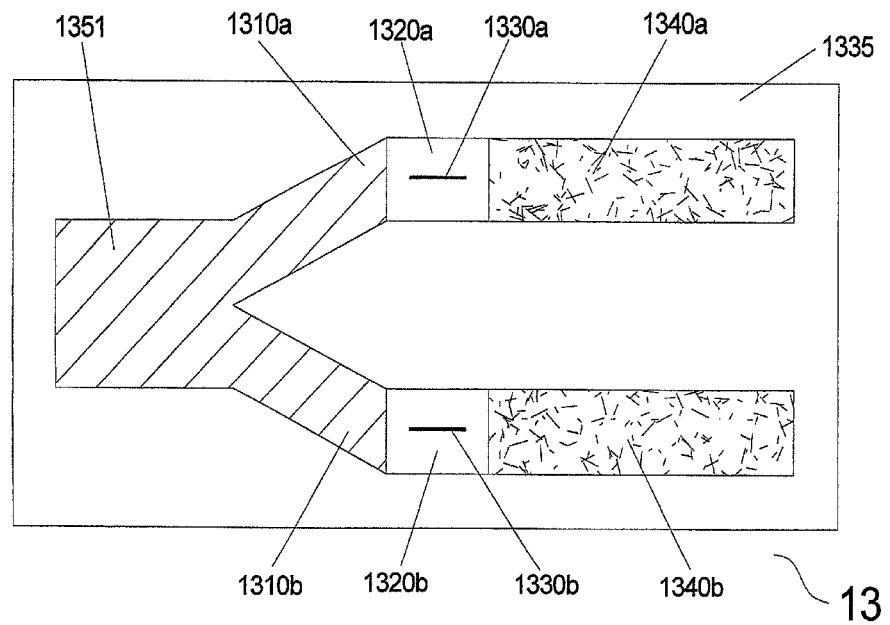
FIG. 13 depicts a cross-section top view of a configuration of the device of the invention, showing a single sample application pad bifurcating to two separate reaction pads and porous membranes, which are each connected to two separate wash solution receiving pads.

FIG. 13 shows a configuration of device 13 of the invention in which a single sample application pad 1351 within container 1335 bifurcates to connect to two separate reaction pads 1310a and 1310b, each of which is at least partially beneath and in contact with a different porous membrane 1320a and 1320b and a different wash solution receiving pad 1340a and 1340 b. Porous membranes 1320a and 1320b comprise specific binding pair members 1330a and 1330 b, each of which are specific for a different substance. In this configuration of the device, the method of the invention can be used to detect two different substances in a single liquid sample. In embodiments, one of the substances is known to be present in the sample (either naturally or as an added component), and thus one membrane (either 1320a or 1320b) acts as a positive control for the device and method.

Figure 14A:
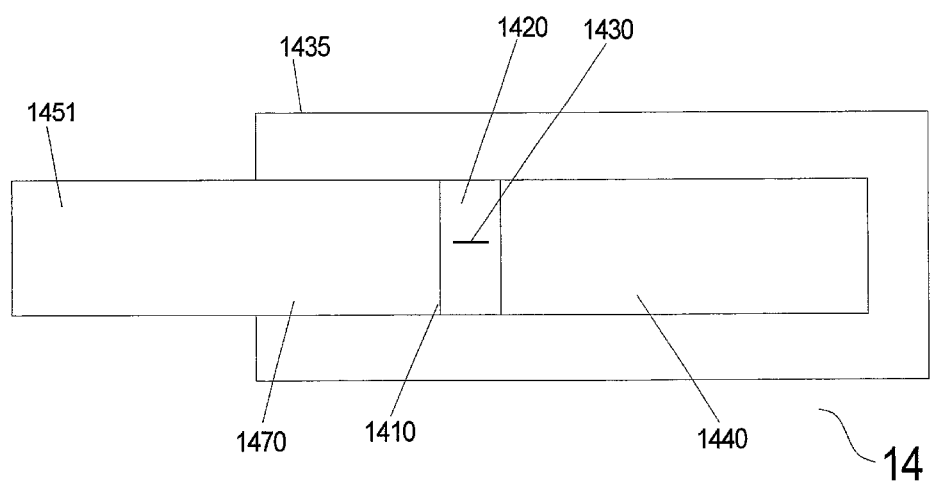
FIG. 14A depicts a top view of a configuration of the device of the invention in which the sample application pad extends beyond the area defined by the container.

FIG. 14A depicts a configuration of device 14 of the present invention in which sample application pad 1451 extends beyond the interior area of device 14 defined by container 1435. Sample application pad 1451 is integral with filtration pad 1470, reaction pad 1410, and wash solution receiving pad 1440. Reaction pad 1410 is at least partially beneath and in direct contact with membrane 1420, which comprises specific binding pair member 1430. In practice of the invention using this configuration of the device of the invention, application pad 1451 is contacted with a liquid sample by dipping into the liquid, inserting into a stream of the liquid (e.g., a stream of urine), application of the sample to the pad by pipetting, or the like. The liquid sample passes through application pad 1451 into filtration pad 1470. In embodiments, a label (not depicted) that binds to the substance of interest is present in filtration pad 1470 and is solubilized by the liquid. The label binds to substance that is present in the sample during passage through filtration pad 1470 (and/or at a later time during the assay). The liquid sample then passes into reaction pad 1410 and diffuses into, through, out, and around membrane 1420. In embodiments, a label that binds to the substance of interest is present in and/or on the surface of reaction pad 1410 and is solubilized by the liquid. The label binds to substance that is present in the sample during passage through reaction pad 1410 (and/or at a later time during the assay). Diffusion from reaction pad 1410 into, through, out, and around membrane 1420 permits contact of the substance of interest (if present) or the substrate-label complex with specific binding pair member 1430. In embodiments where a direct label is used, it can either be bound to the substance at an earlier time (as described immediately above), or can be bound to the substance at the same time or after binding of the substance to the specific binding pair member. Upon formation of a specific binding pair member-substance-label complex, the presence of the substance can be detected. In embodiments where an indirect label is used, the label can be added at any of the times described above. Upon formation of a specific binding pair member-substance-label complex, any excess label and other substances that might be present on the membrane can be washed away by applying a wash solution to membrane 1420. The wash solution passes through membrane 1420 and into reaction pad 1410. Because there is excess wash solution beyond the carrying capacity of reaction pad 1410, liquid is driven into wash solution receiving pad 1440, filtration pad 1470, or both. Because wash solution receiving pad 1440 is typically dry or substantially dry (due to selection of the appropriate amount of volume to be added at application zone 1451) whereas filtration pad 1470 is at least partially wet, wash solution receiving pad 1440 typically absorbs a majority of the wash solution applied to the membrane. The wash may be repeated as many times as necessary to achieve a suitable signal-to-noise ratio. After washing, the substrate for the indirect label can be added, and another wash may be performed, if desired, to reduce background signal. Detection of a specific signal indicates the presence of the substance of interest in the original sample.

Figure 14B:
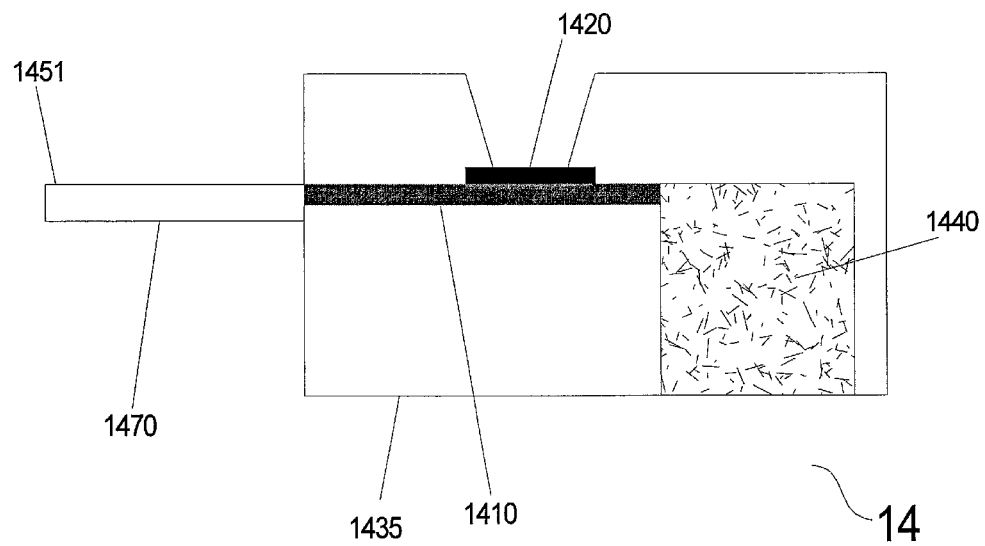
FIG. 14B depicts a cross-section side view of an embodiment of the configuration of the device of the invention depicted in FIG. 14A.

FIG. 14B depicts another embodiment of device 14 depicted in FIG. 14A. In the device of FIG. 14B, applicator pad 1451 comprises an absorbent plastic material onto which a sample, such as urine, comprising an enzyme conjugate that binds to the substance of interest, is applied directly. The sample plus enzyme conjugate travels through filtration pad 1470, which is unitary with application pad 1451, and enters container 1435 through filtration pad 1470, which has been compressed by container 1435. Sample plus enzyme conjugate travels through filtration pad 1470 into reaction pad 1410, which is unitary with filtration pad 1470 and is compressed by container 1435 in a similar fashion as with filtration pad 1470. If a substance of interest is present, it will react with the enzyme conjugate upon mixture before applying, during passage through sample application pad 1451, filtration pad 1470, or reaction pad 1410. The sample is permitted to contact membrane 1420 for a sufficient amount of time for the substance (or the substance-label conjugate complex) to diffuse in, out, and through membrane 1420 and to contact specific binding pair member 1430 (not shown) and form a complex. Wash solution is then applied to membrane 1420 and excess wash solution travels through membrane 1420, and into at least wash solution receiving pad 1440. Detection of the presence or absence of the substance in the sample occurs by detecting a signal produced from membrane 1420 at or near specific binding pair member 1430 (not shown).

Figure 14C:
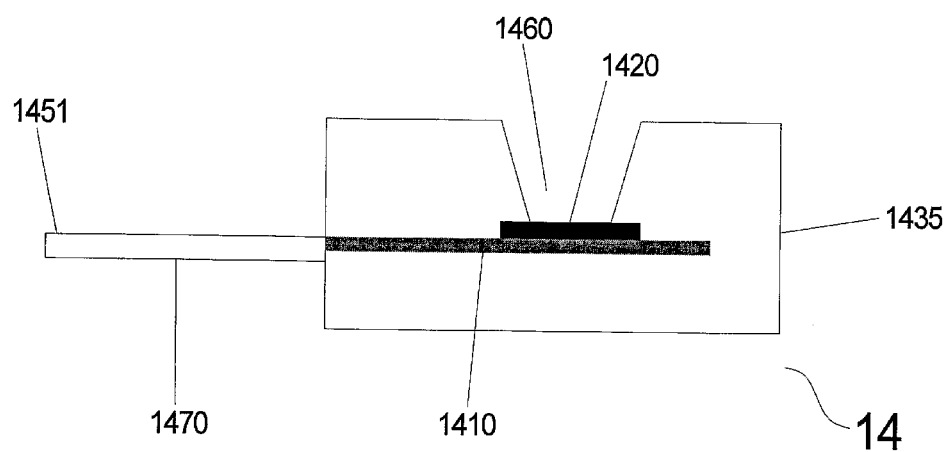
FIG. 14C depicts a cross-section side view of an embodiment of the configuration of the device of the invention depicted in FIG. 14A.

FIG. 14C shows yet another configuration of device 14 depicted in FIGS. 14A and 14B. In this configuration, sample application pad 1451, filtration pad 1470, reaction pad 1410, or a combination of two or all of these comprises a gold conjugate. The gold conjugate, which specifically binds to the substance of interest, is dissolved by the applied liquid sample as it traverses the pads, and binds to the substance, if present. Upon contact of the liquid (now filtered) with membrane 1420 via diffusion in, out, through, and about membrane 1420, the substance-gold conjugate binds to specific binding pair member 1430 (not shown), resulting in generation of a detectable signal at or near specific binding pair member 1430 within about 30 seconds or more of contact of the liquid with membrane 1420. Presence of the substance in the liquid is determined by detection of a signal (typically with the unaided eye) at detection window 1460 without the need for a washing step.

FIG. 15 depicts a configuration of device 15 of the present invention. As shown in FIG. 15A, container 1535 is a "clam shell" type container in which a top half 1535a and a bottom half 1535b are attached to each other along an edge by a flexible hinge 1580.

Although not depicted in the Figure, in embodiments, a holder for a membrane is integral with top half 1535a and defines the edges of a detection window. A sample loading port is also integral to top half 1535a and is defined by an opening in top half 1535a at a site above an application pad. Top half 1535a also comprises one or more pins or recesses to accommodate pins, wherein engagement of the pins with the recesses causes a friction fit that holds top half 1535a and bottom half 1535b together.

In typical embodiments, bottom half 1535b contains a sample application pad, a filtration pad, a reaction pad, and a wash receiving pad. It also typically comprises one or more recesses to accommodate pins or one or more pins, wherein engagement of the recesses with the pins causes a friction fit that holds top half 1535a and bottom half 1535b together.

Figure 15A:
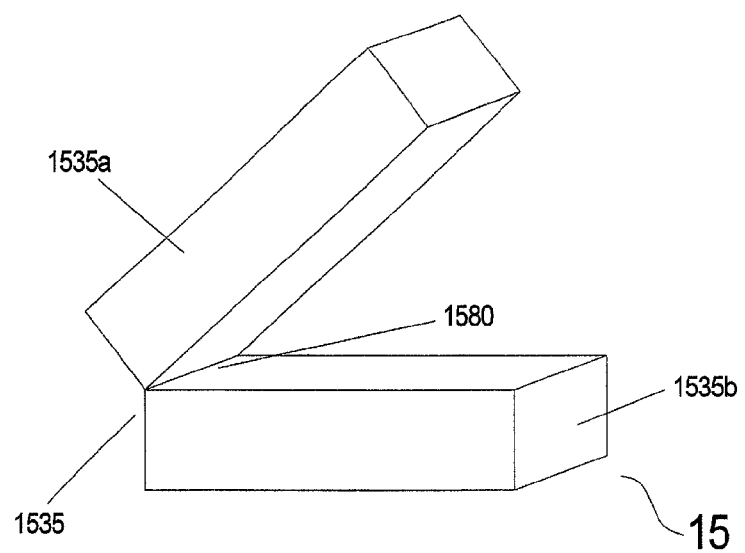
FIG. 15A is a side view of a configuration of the device of the invention in which a "clam shell" container is used.
Figure 15B:
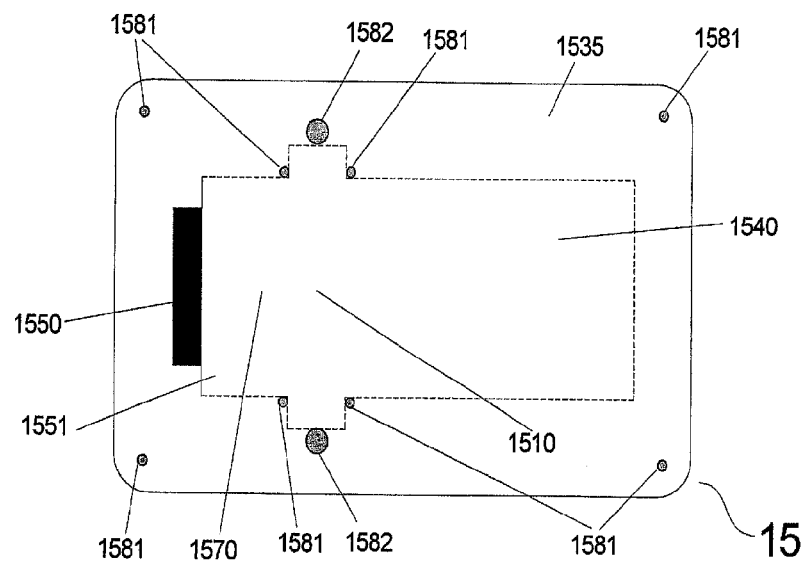
FIG. 15B is a top view of the bottom half of the device depicted in FIG. 15A.

FIG. 15B depicts a top view of the bottom half of one embodiment of device 15 depicted in FIG. 15A. In the Figure, sample application pad 1551 is integral with filtration pad 1570, reaction pad 1510, and wash solution receiving pad 1540, all of which are 2.2 cm wide. Reaction pad 1510 is 0.3 cm wider than sample application pad 1551, filtration pad 1570, reaction pad 1510, and wash solution receiving pad, (0.15 cm on each side) to completely support membrane 1520 (not depicted), which measures 0.75 cm long by 2.5 cm wide). Friction fit alignment post recesses 1581 are present as part of container 1535b, as are clamp posts 1582.

Figure 15C:
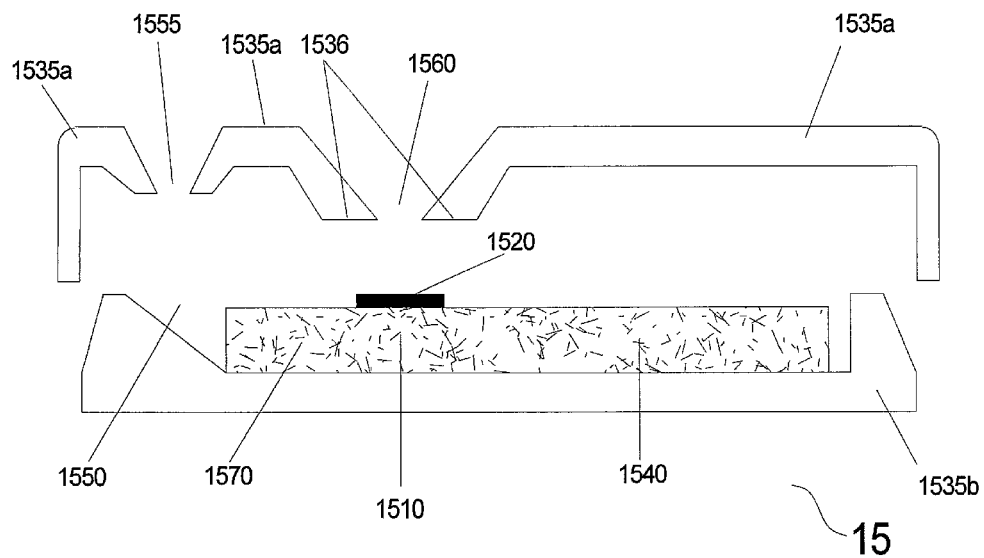
FIG. 15C is a cross-section from the side of the device depicted in FIG. 15A, where the top half is positioned above, but not in contact, with the bottom half, and where the hinge is removed to permit alignment of the top and bottom halves for descriptive purposes.

FIG. 15C shows a cross-section from the side of device 15 depicted in FIG. 15A and/or FIG. 15B, where top half 1535a is positioned above, but not in contact, with bottom half 1535b, and where the hinge is removed to permit alignment of the top and bottom halves for descriptive purposes. The Figure indicates the placement of sample application port 1555 and viewing or detection window 1560.

Figure 15D:
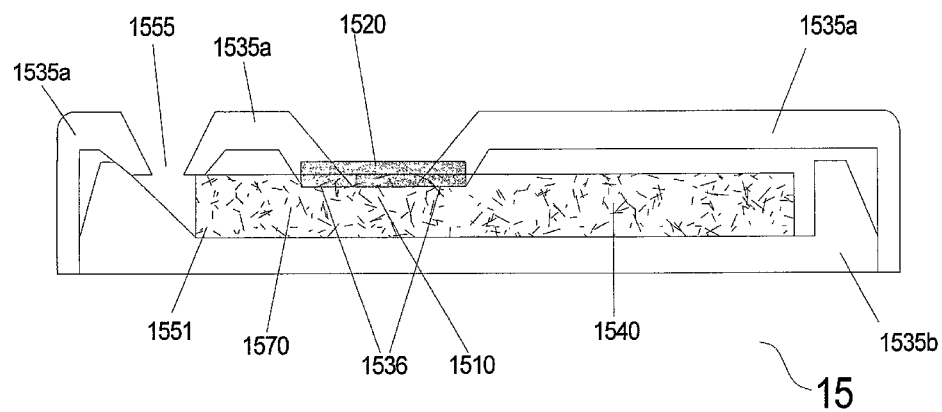
FIG. 15D is a cross-section from the side of the device depicted in FIG. 15A, in which the top half and bottom half are joined by friction fit.

FIG. 15D is a cross-section from the side of device 15 depicted in FIGS. 15A, 15B, and/or 15C, in which the top half and bottom half are joined by friction fit. As can be seen from the Figure, in this embodiment, connection of top half 1535a with bottom half 1535b results in compression of reaction pad 1510 at and near the area where membrane 1520 is in contact with reaction pad 1510.

Figure 16:
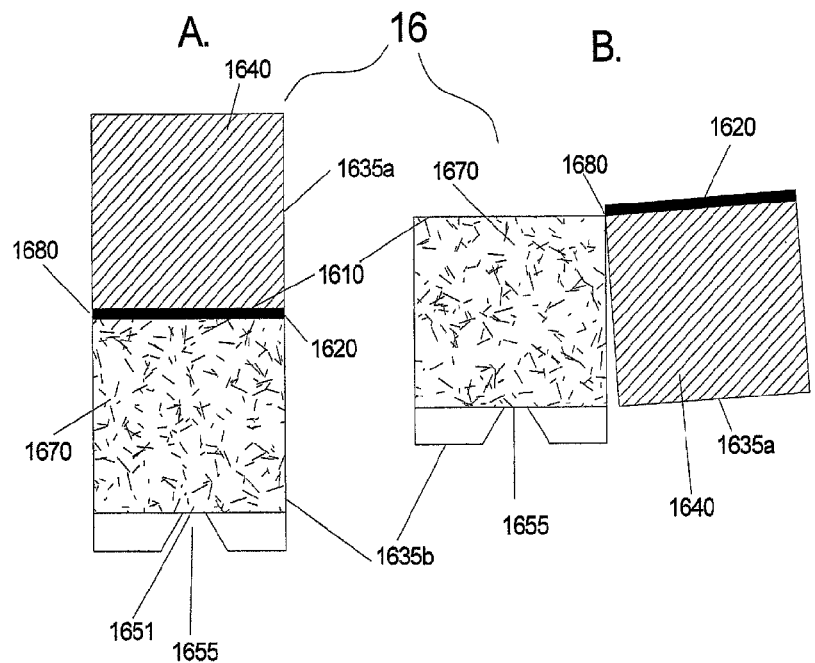
FIG. 16 depicts a cross-section side view of a configuration of the device of the invention in which the device comprises two sections connected by a hinge.

FIG. 16 depicts another embodiment of the device of the invention. In FIG. 16A, the device is depicted in its closed state. In FIG. 16B, the device is depicted in its open state. In this embodiment, device 16 comprises a hinged container of plastic comprising top half 1635a and bottom half 1635 b. Bottom half 1635b comprises sample loading port 1655, and contains a unitary combination of liquid sample application loading pad 1651, filtration pad 1670, and reaction pad 1610. Top half 1635a is attached to bottom half 1635b by a flexible hinge 1680, which is fabricated from the same plastic material as the rest of container 1635. Top half 1635a contains wash solution receiving pad 1640 and porous membrane 1620. Porous membrane 1620 comprises at least one specific binding pair member (not depicted).

When in its closed position, membrane 1620 is sandwiched between reaction pad 1610 and wash receiving pad 1640, and is in contact with both pads, contact being made between reaction pad 1610 and membrane 1620 at least over a portion of membrane 1620 comprising at least one specific binding pair member (not depicted). Sample is applied to application pad 1651 through application port 1655, and sample moves through application pad 1651 and filtration pad 1670 into reaction pad 1610. The portion of the sample present in reaction pad 1610 diffuses into and out of membrane 1620, and contacts the specific binding pair member(s), where the substance of interest, if present, binds to the specific binding pair member(s) and is retained on membrane 1620.

After a sufficient amount of time for reaction of the substance with the specific binding pair member(s), top half 1635a and bottom half 1635b are separated by movement of the two about hinge 1680. If a direct label is used, it may be added at this time, or it may have been present in reaction pad 1610, filtration pad 1670, or application pad 1651, and have already bound to the substance of interest. When a direct label is used, detection of the presence of the substance may be made at this time, or membrane 1620 may be washed to improve signal-to-noise ratio. If a wash is performed, the wash solution is added to membrane 1620, and the wash solution is absorbed (after flowing through membrane 1620) by wash solution receiving pad 1640. If an indirect label is used, the label (or the substrate for the label, if the label has been incorporated into application pad 1651, filtration pad 1670, or reaction pad 1610) is applied to membrane 1620 after separation of top half 1635a and bottom half 1635b, and allowed to remain in contact with membrane 1620 for a sufficient amount of time to react with the specific binding pair member-bound substance. Wash solution is then applied to membrane 1620 as described above. Where necessary, the substrate for the indirect label is then applied to membrane 1620 and allowed to remain in contact for a sufficient amount of time for a complex between the label and label substrate to be formed, or for a detectable signal to be generated.

Figure 17:
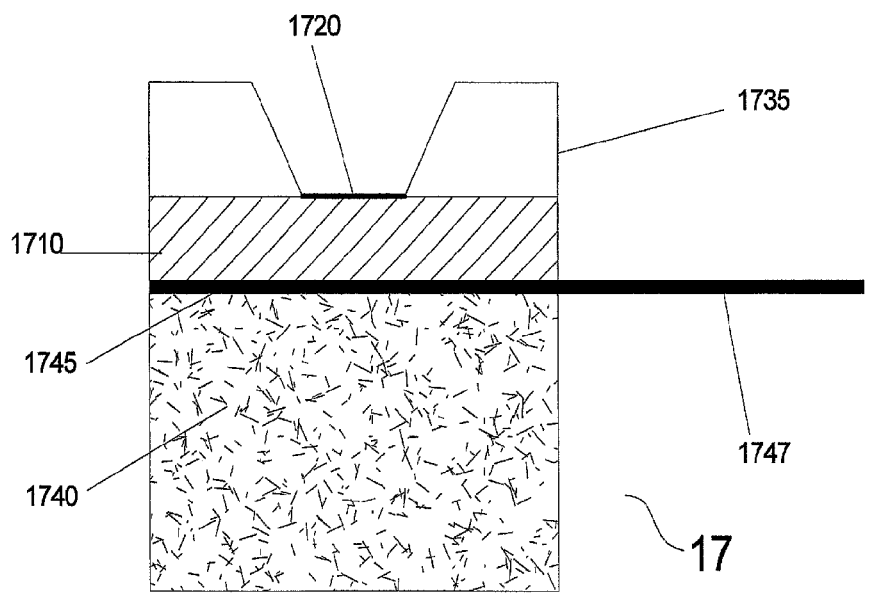
FIG. 17 depicts a side cross-section of a configuration of the device of the invention in which the device comprises an impermeable barrier.

FIG. 17 depicts a device 17, which shows an embodiment of the invention in which a liquid impermeable plastic membrane 1745 is placed between reaction pad 1710 and wash solution receiving pad 1740 within container 1735. In this embodiment, a liquid sample that has been clarified to remove large particulate material, and to which conjugate has been added, is applied to membrane 1720 and permitted to flow into reaction pad 1710, which is in contact with membrane 1720. Sufficient time is provided for diffusion of the sample between reaction pad 1710 and membrane 1720 such that the substance of interest, if present, binds to at least one specific binding pair member (not depicted). After a sufficient amount of time, impermeable barrier 1745 is removed by pulling on tab 1747. Wash solution is applied to membrane 1720, and excess wash solution and unbound substrate, conjugate, and conjugate-substrate complex is washed from membrane 1720 into reaction pad 1710 and then into wash solution receiving pad 1740. Detection of the presence of the substance is then accomplished by direct detection of a signal from or near the specific binding pair member(s) (not depicted), or by addition of substrate for the label. One or more further washings may be performed at this time.

Figure 18:
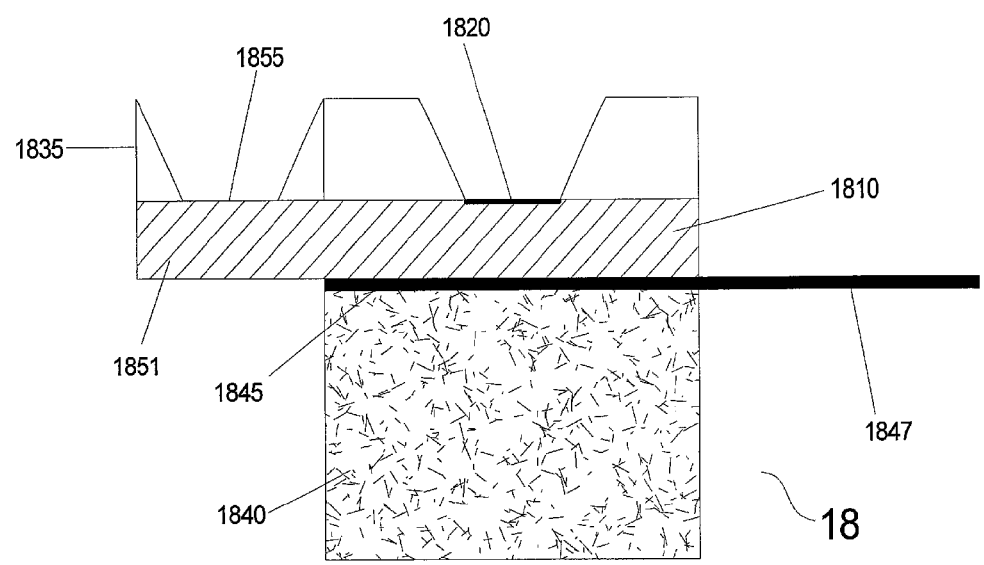
FIG. 18 depicts a side cross-section of a configuration of the device of the invention in which the device comprises an impermeable barrier.

FIG. 18 depicts another configuration of the device of the invention. In this configuration, device 18 comprises container 1835, which comprises sample port 1855 and sample application pad 1851, which are provided adjacent and connected to reaction pad 1810 and membrane 1820. Wash receiving pad 1840 is located below reaction pad 1810 and is separated from reaction pad 1810 by impermeable membrane 1845. Removal of impermeable membrane 1845 by pulling on tab 1847 permits wash solution receiving pad 1840 and reaction pad 1810 to come in direct contact, and provides a continuous flow from membrane 1820 to wash solution receiving pad 1840. In practice, this configuration of the device is used in a similar manner as described with respect to FIG. 17, with the exception that sample is added at sample application port 1855 rather than through membrane 1820.

Figure 19:
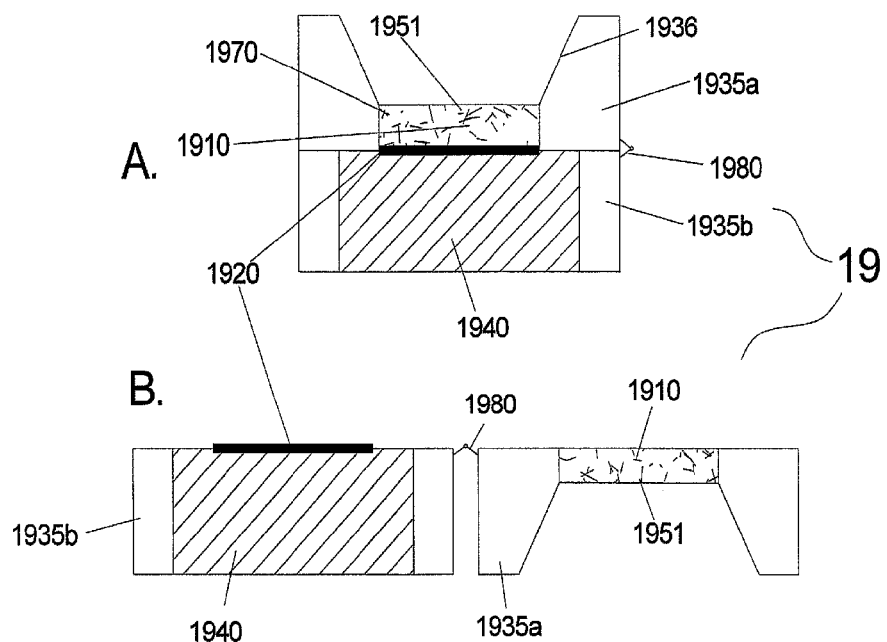
FIG. 19 depicts a side cross-section of a configuration of the device of the invention in which the device comprises a hinge connecting the top and bottom halves. Panel A depicts the device in a closed position for sample application and binding. Panel B depicts the device in an open position for reading reaction results.

FIG. 19 depicts an embodiment of the invention similar to that depicted in FIG. 16. FIG. 19A depicts the device in a closed position. FIG. 19B depicts the device in an open position. As can be seen in FIG. 19A, device 19 comprises a container comprising upper half 1935a and lower half 1935b, connected via a hinge 1980. Upper half 1935a comprises reaction pad 1910, which is integral with sample application pad 1951, and which is held in place by holder 1936. Membrane 1920 is located in between reaction pad 1910 and wash receiving pad 1940, in direct physical contact with both through pressure exerted on membrane 1930 by holder 1936. Bottom half 1936b comprises wash receiving pad 1940, in direct physical contact with membrane 1920. In practice of one embodiment of the method of the invention with this configuration of the device, as depicted in the combination of FIG. 19A and FIG. 19B, sample (to which a label conjugate has been added) is applied to application pad 1951 (which is integral with reaction pad 1910 and filtration pad 1970), and liquid of the sample is permitted to travel to reaction pad 1910 and diffuse into and out of membrane 1920. Wash solution is added to sample application pad 1951 and is drawn through reaction pad 1910 and membrane 1920 by drawing of the liquid into wash solution receiving pad 1940 as a result of its being dry. Substrate for the label conjugate is then applied to membrane 1420 and the two halves 1935a and 1935b are separated by rotation about hinge 1980, thus revealing membrane 1920. The presence of the substance is detected by visual or non-visual detection methods by assaying for signal emitted from or near at least one specific binding pair member (not depicted) spotted on membrane 1920.

Figure 20:
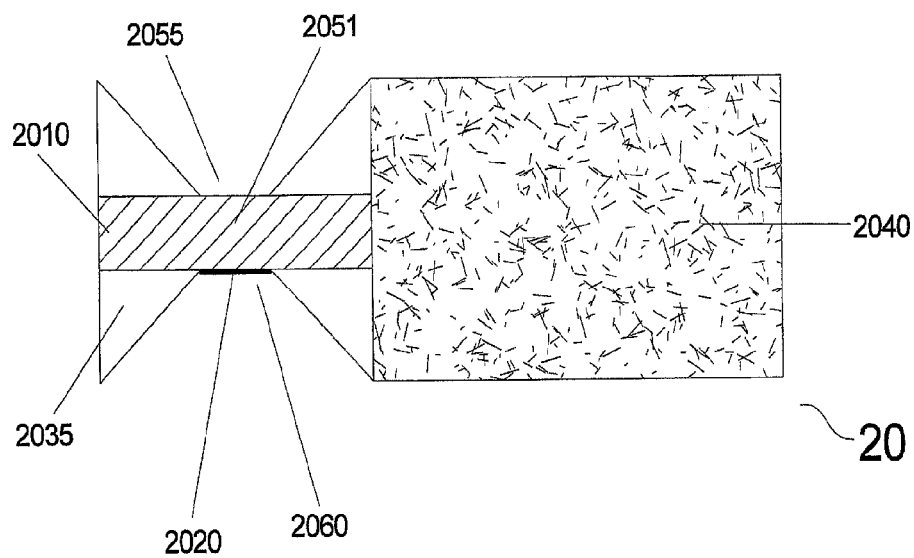
FIG. 20 depicts a side cross-section of a configuration of the device of the invention in which the device comprises an application port at the bottom of the device and a wash solution receiving pad on the side.

FIG. 20 is a configuration of device 20 of the invention comprising container 2035, and in which application pad 2051 is integral with reaction pad 2010, and in which application port 2055 is located above/beneath and on the opposite side of membrane 2020 and detection window 2060. Wash solution receiving pad 2040 is in direct contact with application pad 2051 and reaction pad 2010 and is located to the side of these pads, with respect to application port 2055 and detection window 2060. In practice of an embodiment of the method of the invention with this configuration of the device, sample (to which conjugate has been added) is applied to application pad 2051 through application port 2055, and sample is allowed to traverse into reaction pad 2010, and diffuse between reaction pad 2010 and membrane 2020, which comprises at least one specific binding pair member (not depicted). Device 20 is inverted after the liquid sample has been fully or substantially fully drawn into application pad 2051 and reaction pad 2010, and a desired amount of diffusion between pad 2010 and membrane 2020 has occurred. Wash solution is applied to membrane 2020, and drawn through reaction pad 2010 and application pad 2055 into wash receiving pad 2040. Substrate for the conjugate is added and detection of the presence of the substance of interest in the liquid is performed, in accordance with known procedures and the disclosure above. As with all other embodiments where an indirect label is used, incubation of the substrate and the label is preferred to obtain optimal signal intensity.

Figure 21:
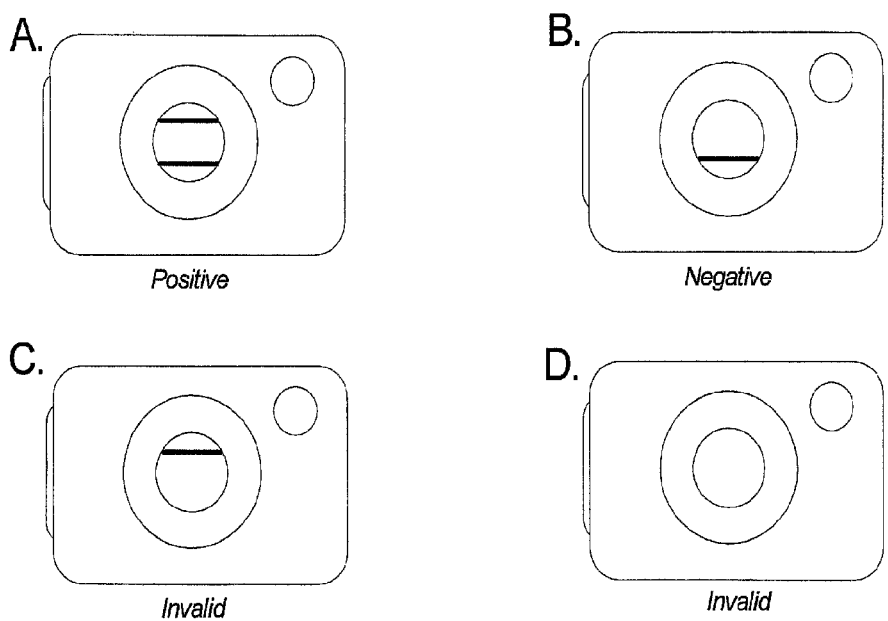
FIG. 21A depicts a top view of a configuration of the device of the invention, as it would look when a positive sample were detected.
FIG. 21B depicts a top view of a configuration of the device of the invention, as it would look when a negative sample were detected.
FIG. 21C depicts a top view of a configuration of the device of the invention, when the device and/or method failed.
FIG. 21D depicts a top view of a configuration of the device of the invention, when the device and/or method failed.

FIG. 21 depicts one embodiment of the device of the invention, which is also referenced in an Example below. In general, the embodiment comprises the elements discussed above with regard to other embodiments. In one particular embodiment of the device depicted in FIG. 21, the device comprises a reaction window opening onto a porous membrane comprising two lines of immobilized antibodies spotted thereon. For example, it can contain a test line (or "T" line), having antibodies against *C. difficile* toxin A, toxin B, or both. It can also contain a second line (or "C" line) to act as an internal control, for example having anti-IgG antibodies or other antibodies specific for other antigens. In use, the device can detect the presence of a substance of interest, such as toxin A and/or B, in a sample. For example, a sample can be added to a tube containing a mixture of a diluent (e.g., a buffered protein solution containing 0.02% thimerosal) and conjugate (e.g., a mouse monoclonal antibody specific for toxin A coupled to horseradish peroxidase and a goat polyclonal antibody specific for toxin B coupled to horseradish peroxidase in a buffered protein solution containing 0.02% thimerosal). The diluted sample-conjugate mixture can then be added to a sample well, which is an opening in the shell of the device, and which opens onto a porous material (filter pad) in an area for receiving the sample, which is distinct from the reaction window. After adding the diluted sample to the porous material through the sample well, the device can be incubated at a suitable temperature, for example at room temperature, for a sufficient amount of time, for example 15 minutes. During this incubation period, the substance of interest (e.g., toxin A and/or B), if present in the sample, binds to the conjugate (e.g., anti-toxin antibody-peroxidase conjugate). After application of the sample to the device, the substance-conjugate (e.g., toxin-antibody) complexes, if present, migrate through at least one porous material to the porous membrane containing the immobilized antibodies. A sufficient amount of time (e.g., one minute) is provided for diffusion of the complexes in and out of the porous membrane. Complexes, if present, are captured by the immobilized antibodies on the line(s). The porous membrane, at least at the area comprising a portion of the lines, can then be optionally washed with a wash buffer (e.g., a buffered solution containing 0.02% thimerosal). The device can then be developed with the addition of a substrate (e.g., a solution comprising tetramethylbenzidine). After an incubation period (for example, 10 minutes), the presence of a complex at the test line can be determined by, for example, visually examining for the appearance of a line (e.g., a blue line) at the area where the "T" line is present on the porous membrane below the reaction window. A line at this area indicates a positive test. Where a line (e.g., blue line) exists at the "C" area of the porous membrane below the reaction window, a positive control reaction has occurred, indicating that the device and method are working properly, and that the results (presence or absence of substance of interest) are valid. Where a control is run, the control can include an appropriate antigen for an antibody spotted onto the membrane at the "C" line, such as an antigen in a buffered aqueous solution. FIG. 21A-D depict the lines described herein, and note various possible results.

Thus, the invention provides a method of detecting at least one substance of interest in a liquid sample, where the method comprises: providing a liquid sample comprising or suspected of comprising the substance(s) of interest; applying the liquid sample to a porous material in a sufficient amount to at least partially wet the porous material; contacting the porous material with a porous membrane comprising at least one specific binding pair member that is capable of binding, either directly or indirectly, the substance(s) of interest; maintaining the porous material and porous membrane in contact for a sufficient amount of time for liquid present in the porous material to diffuse in, out, through, and/or about the porous membrane, wherein diffusion of the liquid in, out, through, and/or about the porous membrane results in contact of the substance(s) of interest, if present, to be bound, either directly or indirectly, to the specific binding pair member(s); and detecting the presence or absence of a complex comprising the specific binding pair member(s) and the substance(s) of interest, wherein the presence of at least one complex indicates the presence of at least one of the substances of interest in the liquid sample. In embodiments, the method can further comprise providing a device comprising the porous material and porous membrane. In embodiments, the porous material filters the liquid sample to remove substances having a size greater than a pre-determined value. In embodiments, the filtering is by way of discontinuous wicking of liquid from the liquid sample through the porous material. In embodiments, the method can be used in conjunction with a liquid that comprises two or more substances of interest, and one, two, or more of these substances can be detected using a single device and/or a single practice of the method of the invention. Thus, in certain embodiments of the method, each substance of interest is different than each other substance of interest, and the method detects one, two, or more of them. The method can be practiced on liquid samples containing feces, blood, food, or an environmental sample (e.g., a toxic substance in ground water). In exemplary embodiments, the method detects one or both of *Clostridium difficile* toxin A and *Clostridium difficile* toxin B. In embodiments, the substance of interest is one or more toxin, bacterium, virus, bacterial product, enzyme (e.g., prokaryotic, eukaryotic), or parasite. In some embodiments, the substance of interest is glutamate dehydrogenase. It can also be an animal or human product, an antibody, or lactoferrin.

The method can be practiced using one or more specific binding pair members. In embodiments, one or more of the specific binding pair member(s) is an antibody, wherein each of the antibodies is either different or the same as one or more others.

The general method can further comprise washing the membrane prior to detecting the presence of a complex.

In embodiments, applying the liquid sample to the porous material comprises applying the liquid sample at a location on the porous material that is spatially separated from the porous membrane, whereby at least the liquid of the liquid sample travels into the porous material and then the porous membrane. In certain embodiments, liquid sample that is applied at a region of a sample loading zone that is distant from a detection zone travels through the porous material to the porous membrane through a wicking process. In embodiments, a physical force is applied to the membrane, the porous material, or both, and such a force improves sensitivity of the device and method of the invention.

The method of the invention comprises detecting a signal to determine the presence of a substance of interest. In embodiments, detecting comprises observing a signal emitted from a label bound to the substance of interest. In particular embodiments, the signal is produced by a colored precipitating product that forms in or around the specific binding pair member. Detecting thus can be through detection of a complex. Therefore, the method can comprise combining a labeled conjugate with the liquid sample prior to applying the liquid sample to the porous material. The labeled conjugate can comprise a latex bead or other colored particle, a colloidal gold particle, or a reactive substance that binds to a substrate to create a detectable signal. In some embodiments, the signal is a non-visual signal.

The invention includes a device for detecting at least one substance of interest in a liquid sample. In embodiments, the device comprises: (a) a receptacle comprising a porous material for receiving the liquid sample, wherein the porous material is capable of absorbing and transmitting at least a portion of the liquid sample, and (b) a porous membrane that comprises a specific binding pair member that is specific for the substance of interest or a substance bound to the substance of interest, wherein the receptacle and porous membrane are each shaped to permit the porous membrane to be in direct contact with the porous material over at least a portion of the porous membrane that comprises the specific binding pair member. The device can comprise a container containing the receptacle, a holder for the porous membrane, a wash solution receiving pad, a liquid sample application pad, a filtration pad, or two or more of these elements. Each element may be subdivided into two or more functional zones, which, while optionally being fabricated of the same material, can be fabricated from different materials than one or more of the other zones.

In embodiments, the device comprises a container containing a reaction pad comprising the porous material and the porous membrane, the container comprising a holder for the porous membrane, wherein the container causes pressure to be exerted on the porous membrane and/or the porous material such that at least a portion of the porous material is compressed. Of course, the container can contain other elements, as discussed above. Compression of the porous material can cause the porous membrane and the porous material to be in direct contact over at least a portion of the porous membrane, and can improve the function of the device and method of the invention. For example, the pressure can permit one or more liquids to pass between the porous membrane and the porous material by passive diffusion.

The invention thus provides a device for detecting at least one substance of interest in a liquid sample, where the device comprises: (a) a receptacle comprising a porous material for receiving the liquid sample, wherein the porous material is capable of absorbing and transmitting at least a portion of the liquid sample, and (b) a porous membrane that comprises a specific binding pair member that is specific for the substance of interest or a substance bound to the substance of interest, wherein the receptacle and porous membrane are each shaped to permit the porous membrane to be in direct contact with the porous material over at least a portion of the porous membrane that comprises the specific binding pair member, wherein the porous membrane and porous material are different elements having a different chemical constitution. In embodiments, the porous membrane and porous material are in physical contact such that liquid sample applied to the porous material diffuses in, out, through, and about the porous membrane. In addition, the device may be constructed such that physical contact between the porous membrane and porous material is created such that the sensitivity of the device is improved. The device can be configured such that the porous material and porous membrane are in contact with each other such that the substance of interest does not need to traverse the porous membrane in a unidirectional manner for the device to detect the substance of interest. In exemplary embodiments, the porous material and porous membrane are in contact with each other in such a way to permit simple, non-directional diffusion of a liquid between the two to occur.

The invention thus provides a device for detecting the presence or amount of a substance of interest in a liquid sample, where the device comprises: a sample receiving zone for receiving the liquid sample, wherein the sample receiving zone is present on a porous material; a sample filter zone for filtering the liquid sample received at the sample receiving zone, wherein the sample filtering zone is present on a porous material; a porous membrane comprising a specific binding member at a detection zone that specifically binds to the substance of interest or a substance bound to the substance of interest, wherein the porous membrane is not the same element as any of the porous materials, and wherein the porous material and porous membrane are in physical contact over at least an area comprising a portion of the detection zone, and wherein the porous material and porous membrane are in physical contact in a configuration that permits liquid present in the liquid sample to diffuse in, out, through, and about the porous membrane in a substantially random, non-directional manner in an area comprising at least a portion of the detection zone. Of course, one or more zones can be present on a single porous material or on two or more different materials. Likewise, they can be present on two or more different materials, each independently selected to have the same or different composition as one or more other. As mentioned above, the device may comprise a container that contains at least a portion of the porous material(s) and porous membrane. In embodiments, the device comprises a porous material comprising a wash solution receiving zone.

Other exemplary embodiments of the device of the invention, and use of the device in practice of the method of the invention, are provided in the Examples that follow and others will be apparent from the description and drawings.

EXAMPLES

The invention will be further explained by the following Examples, which are intended to be purely exemplary of the invention, and should not be considered as limiting the invention in any way.

Example 1

Use of an Embodiment of the Device and Method of the Invention

This Example details a typical in vitro use and guidelines for in vitro use of an embodiment of the method of the invention in an embodiment of the device of the invention, as depicted in FIGS. 21A-D, in which *Clostridium difficile* Toxins A and B are detected. The protocol generally follows the protocol provided in the TOX A/B QUIK CHEK™ kit (TechLab, Blacksburg, Va.; cat. no. T5033), which is incorporated herein in its entirety by reference. Unless otherwise noted, the protocol provided in the TOX A/B QUIK CHEK™ kit was use in the Examples. General guidelines are provided in this Example and in the TechLab kit, but are not necessarily applicable to other embodiments of the method of the invention.

Collection and Handling of Fecal Specimens

Standard collection and handling procedures used for fecal specimens are appropriate. Specimens should be stored between 2° C. and 8° C. It is preferred to test specimens that are less than 24 hours old. It is preferred to store specimens frozen (less than or equal to −10° C.) if the test cannot be performed within 72 hours of collection. While data shows that one freeze-thaw cycle does not harm the sample for use with *C. difficile* toxins A and B, it is noted that freezing and thawing of a specimen, especially multiple times, might result in loss of activity due to degradation of the toxins. Fecal specimens that have been preserved in 10% Formalin, MF, SAF, or PVA, or specimens that are in transport media such as Cary Blair or C&S typically do not give as optimal results as fresh samples or those preserved in other compositions.

Specimens should be thoroughly mixed (e.g., vortexed) prior to performing the assay. Storing of fecal specimens in the diluent is not recommended. It is preferred that one immediately test a sample once the fecal specimen is diluted in diluent. Disposable pipettes graduated at 50, 100, 200, and 300 ul may be used.

Sample Preparation optionally bring all reagents and devices to room temperature before use.

Set up one cassette (device) for each specimen to be tested.

Add 0.4-0.6 ml (e.g., 0.425 ml or 0.5 ml) diluent to each dilution tube using a plastic dropper.

Evenly suspend (e.g., vortex) the specimens before transferring. For Liquid/Semi-solid specimens, draw the specimen halfway to the first mark from the end (25 ul). Dispense the specimen into the diluent. Use the same pipette to mix the diluted specimen by gently aspirating, then dispensing the mixture several times. For Formed/Solid specimens, mix the specimen thoroughly. Using a wooden applicator stick, transfer a small portion (approximately 2 mm diameter) of the specimen into the diluent. Emulsify the specimen using the applicator stick. As an optional control, add 1 drop of positive control or negative control (specimen diluent) to tubes containing 0.4 ml diluent.

Add 1 drop of conjugate to the diluted specimen and mix the tube contents by vortexing.

Test Procedure

Obtain the required number of cassettes, one per specimen, and one per positive or negative control. Label the membrane cassettes appropriately.

Obtain the prepared samples. Using a disposable transfer pipette, transfer 300-400 ul of the diluted sample-conjugate mixture into the sample port of the cassette and incubate the cassette at room temperature for 15 minutes. An increasing wet area will be visible in the results window. If no wet area appears in the results window, add 100 ul of diluent to the sample port and wait an additional 5 minutes.

After 15 minutes, add 300 ul of wash buffer to the reaction port. Allow the wash buffer to enter the reaction port completely.

Add 2 drops of substrate to the reaction port and allow the cassette to incubate at room temperature for 10 minutes. At the end of 10 minutes, read the results from the detection window. Observe for the appearance of a colored (e.g., blue) line representing the control line (see FIG. 21A). The lines may appear faint to dark in color.

Interpretation of Results

Positive Result (FIG. 21A): Two lines are visible, one on the bottom of the reaction port (control line) and one on the top of the reaction port (test line). A positive result indicates the presence of *C. difficile* toxin and a properly reactive control.

Negative Result (FIG. 21B): A single control line is visible only on the bottom of the reaction port. No test line is visible on the top of the reaction port. A negative result indicates the absence of *C. difficile* toxin but a properly reactive control.

Invalid Result (FIGS. 21C and 21D): All completed reactions should have a visible control line on the bottom of the reaction port. The test is invalid if a control line is not present on the completed cassette.

Example 2

Comparison of Detection of *Clostridium difficile* Toxins A and B Using the Device of the Invention and Tissue Culture An embodiment of the device of the invention was used to detect a combination of *C. difficile* toxin A and toxin B in 50 fecal samples, and the results compared to results obtained for the same samples using tissue culture methods. Tissue culture detection of *C. difficile* toxin in fecal samples is the art-recognized assay of choice because it is considered to be the most sensitive method for detecting the toxins. The method described in Example 1 was used to detect the toxins.

The tissue culture test was the *C. difficile* Tox-B Test kit manufactured by Tech Lab, Inc. (cat. no. T5003), and the procedure was as described in the product insert. In brief, fecal samples were diluted 1:10 in diluent and filtered through a 0.45 micron sterile filter. Each fecal sample was added (50 microliters) to each of two tissue culture wells. One well received 50 microliters of antitoxin to neutralize *C. difficile* toxins A and B and the other well received 50 microliters of only phosphate buffered saline. The human foreskin tissue cultured cells were incubated at 37° C. for 24 hours then examined for rounding of the cells, and examined again at 48 hrs. Wells in which greater than 50% of the cells were rounded were considered positive. For a positive overall reaction, the well containing antitoxin had to be normal while the well without antitoxin showed rounding of the cells.

Table 1 shows the results of the assays, and compares the results of the method and device of the present invention with the tissue culture assay.

TABLE 1

| N = 50 | A/B Invention pos | A/B Invention neg |
|---|---|---|
| Tiss cult pos | 8 | 0 |
| Tiss cult neg | 1 | 41 |
| Sensitivity | 88.9 | |

TABLE 1-continued

| N = 50 | A/B Invention pos | A/B Invention neg |
|---|---|---|
| Specificity | 100.0 | |
| Pred Pos Val | 100.0 | |
| Pred Neg Val | 97.6 | |
| Correlation | 98.0 | |

The results indicate that a device and method of the present invention perform almost identically to tissue culture.

Example 3

Comparison of Detection of *Clostridium difficile* Toxins A and B Using the Device of the Invention and ELISA A device of the invention was used to detect a combination of *C. difficile* toxin A and toxin B in 50 fecal samples, and the results compared to results obtained for the same samples using ELISA. The method described in Example 1 was used to detect the toxins.

The TechLab Inc. Tox A/B Test kit was used in this experiment according the directions in the product insert. Briefly, feces were diluted 1:5 in sample diluent and 100 microliters were added to wells in an ELISA 96 well plate. Then 50 microliters of conjugate solution (containing antibodies to *C. difficile* toxins A and B that had been conjugated to horseradish peroxidase) was added to each well. Wells were incubated 50 min at 37° C. and then the wells were washed to remove horse radish peroxidase conjugate that had not bound to toxins (that had bound to antibodies coating the wells). This sandwich of antibodies and enzyme was then detected by addition of 100 microliters of substrate solution with incubation for 10 minutes followed by addition of 50 microliters of dilute acid to stop the reaction. Positive reactions were those wells with an Optical Density at 450 nm of greater than 0.12.

Table 2 shows the results of the assays, and compares the results of the method and device of the present invention with the ELISA assay.

TABLE 2

| N = 50 | A/B Invention pos | A/B Invention neg |
|---|---|---|
| Tiss cult pos | 8 | 1 |
| Tiss cult neg | 1 | 41 |
| Sensitivity | 88.9 | |
| Specificity | 97.6 | |
| Pred Pos Val | 88.9 | |
| Pred Neg Val | 97.6 | |
| Correlation | 96.0 | |

The results indicate that the device and method of the present invention produce results that are comparable to the sensitive ELISA method used.

Example 4

Investigation of Relative Sensitivity of a Device and Method of the Invention

The sensitivity of a device and method of the invention was determined. The device and method used were that of the TOX A/B QUIK CHEK™ test for toxins A and B (TechLab, Inc.). Briefly, the sensitivity of the device and method was determined using serial two-fold dilutions of highly purified toxins A and B.

The test was consistently positive at a concentration of 0.63 ng/mL for toxin A and 1.25 ng/mL for toxin B. The results of six separate tests (Tests 1 through 6) with serially diluted toxin A or toxin B for the test are shown in the tables below.

TABLE 3

Reaction of highly purified toxin A in the TOX A/B QUIK CHEK ™ test

| Conc. (ng/ml) | Test 1 | Test 2 | Test 3 | Test 4 | Test 5 | Test 6 |
|---|---|---|---|---|---|---|
| 1.25 | + | + | + | + | + | + |
| 0.63 | + | + | + | + | + | + |
| 0.32 | + | + | − | + | +/− | +/− |
| 0.16 | − | − | +/− | − | − | − |
| 0.08 | − | − | − | − | − | − |

TABLE 4

Reaction of highly purified toxin B in the TOX A/B QUIK CHEK ™ test

| Conc. (ng/ml) | Test 1 | Test 2 | Test 3 | Test 4 | Test 5 | Test 6 |
|---|---|---|---|---|---|---|
| 1.25 | + | + | + | + | + | + |
| 0.63 | − | − | − | − | + | + |
| 0.32 | − | − | − | − | − | − |
| 0.16 | − | − | − | − | − | − |
| 0.08 | − | − | − | − | − | − |

The data presented in Tables 3 and 4 are representative of the particular results obtained in the particular testing runs performed. In other tests, sensitivity of 0.16 for Toxin A and 0.32 to 0.63 for Toxin B has been often seen.

Example 5

Reproducibility and Precision of an Apparatus and Method of the Invention

To determine the reproducibility and precision of devices and methods of the invention, an embodiment of the device of the invention, as depicted in FIG. 21, was testing using an embodiment of the method of the invention, according to a protocol supplied with the TechLab TOX A/B QUIK CHEK™ test. More specifically, a total of 8 fecal specimens, 6 positive and 2 negative, were tested in three different laboratories using the TOX A/B QUIK CHEK™ test (TechLab, cat. no. T5033) according to the manufacturer's instructions. To challenge the cutoff, 2 weakly positive specimens that gave faint lines when analyzed by the inventors were included in the 6 positive specimens. All of the specimens were classified by a predicate device, the *C. Difficile* TOX A/B II™ test (TechLab; cat. no. T5003), which is widely accepted as a highly sensitive and accurate test for the presence of *C. difficile* toxins A and B. All specimens were kept frozen at ≦−10° C. until the assay was performed. Each of the laboratories tested the specimens on 3 different days. The results from each laboratory were subsequently submitted to the inventors and compared with the inventors' own results. The results, shown below, were consistent among the different locations, and exhibited a correlation of 100%. The positive specimens were confirmed to be positive and the negative specimens were confirmed to be negative at all sites using the TOX A/B QUIK CHEK™ test.

TABLE 5

Reproducibility/Precision Testing By Inventors Of Fecal Samples Using A Device And Method According To The Invention

| Specimen Code (n = 8) | TOX A/B II™ ELISA | Day 1 | Day 2 | Day 3 |
|---|---|---|---|---|
| TL001 | + | + | + | + |
| TL002 | + | + | + | + |
| TL003 | + | + | + | + |
| TL004 | + | + | + | + |
| TL005 | + | + | + | + |
| TL006 | + | + | + | + |
| TL007 | − | − | − | − |
| TL008 | − | − | − | − |
| Percent Correlation | N/A | 100 | 100 | 100 |

TABLE 6

External Reproducibility/Precision Testing Of Fecal Samples Using A Device And Method According To The Invention

| Specimen Code (n = 8) | TOX A/B II™ ELISA | Day 1 | Day 2 | Day 3 |
|---|---|---|---|---|
| TL001 | + | + | + | + |
| TL002 | + | + | + | + |
| TL003 | + | + | + | + |
| TL004 | + | + | + | + |
| TL005 | + | + | + | + |
| TL006 | + | + | + | + |
| TL007 | − | − | − | − |
| TL008 | − | − | − | − |
| Percent Correlation | N/A | 100 | 100 | 100 |

TABLE 7

External Reproducibility/Precision Testing Of Fecal Samples Using A Device And Method According To The Invention

| Specimen Code (n = 8) | TOX A/B II™ ELISA | Day 1 | Day 2 | Day 3 |
|---|---|---|---|---|
| TL001 | + | + | + | + |
| TL002 | + | + | + | + |
| TL003 | + | + | + | + |
| TL004 | + | + | + | + |
| TL005 | + | + | + | + |
| TL006 | + | + | + | + |
| TL007 | − | − | − | − |
| TL008 | − | − | − | − |
| Percent Correlation | N/A | 100 | 100 | 100 |

TABLE 8

External Reproducibility/Precision Testing Of Fecal Samples Using A Device And Method According To The Invention

| Specimen Code (n = 8) | TOX A/B II™ ELISA | Day 1 | Day 2 | Day 3 |
|---|---|---|---|---|
| TL001 | + | + | + | + |
| TL002 | + | + | + | + |
| TL003 | + | + | + | + |
| TL004 | + | + | + | + |
| TL005 | + | + | + | + |
| TL006 | + | + | + | + |
| TL007 | − | − | − | − |
| TL008 | − | − | − | − |
| Percent Correlation | N/A | 100 | 100 | 100 |

As can be seen, the device and method performed well in the hands of four different practitioners.

Example 6

Effect of Freeze-Thaw on Specimens

To further characterize devices and methods according to the invention, an embodiment of the device was used in conjunction with a method according to the invention to determine the suitability of each with specimens that had been subjected to at least one freeze-thaw cycle.

A total of eight fecal specimens, consisting of 6 positive and 2 negative specimens, were tested using an embodiment of the device of the invention, as depicted in FIG. 21, and an embodiment of the method of the invention, both of which are available in the TOX A/B QUIK CHEK™ test from TechLab, Inc. (cat. no. T5033) before and after a single freeze-thaw cycle. The specimens had been tested previously in the *C. Difficile* TOX A/B II™ (TechLab, Inc.; cat. no. T5003) test for the presence or absence of toxins A and B. The results are shown in the table below. Included is the residual reactivity in the *C. Difficile* TOX A/B II™ test after the freeze-thaw cycle. The results showed that the positive specimens remained positive after the freeze-thaw cycle and the negative specimens remained negative. No conversion of positive-to-negative or negative-to-positive was observed in any of the specimens.

TABLE 9

Effect of Freeze-Thaw Cycle on Device and Method of the Invention

| Specimen Code (n = 8) | TOX A/B II™ ELISA (before freezing) | INVENTION (before freezing) | TOX A/B II™ ELISA (after freezing) | INVENTION (after freezing) |
|---|---|---|---|---|
| TL001 | + | + | + | + |
| TL002 | + | + | + | + |
| TL003 | + | + | + | + |
| TL004 | + | + | + | + |
| TL005 | + | + | + | + |
| TL006 | + | + | + | + |
| TL007 | − | − | − | − |
| TL008 | − | − | − | − |

Example 7

Effect of Specimen Storage Between 2° and 8° C. for 72 Hours

To further investigate the use of the device and method of the invention for detection of substances of interest in samples, six positive and two negative fecal specimens (with respect to *C. difficile* toxins A and B) were tested at times 24, 48, and 72 hours using a device and method according to the present invention, specifically in the TOX A/B QUIK CHEK™ test (TechLab, Inc.; cat. no. T5033) according to the manufacturer's instructions, to evaluate the stability of the toxins in fecal samples. The results, shown below, demonstrate that the device and method performed consistently at each time interval. In addition, it shows that the C. difficile toxins are stable for at least 72 hours under these test conditions. All of the positive specimens remained positive and the negative specimens remained negative at each time period.

TABLE 10

Effect of Specimen Storage Between 2° and 8° C. for 72 Hours

| Specimens (n = 8) | Day 1 C. difficile TOX A/B II ™ 20 min assay | Day 1 TOX A/B QUIK CHEK ™ | Day 2 C. difficile TOX A/B II ™ | Day 2 TOX A/B QUIK CHEK ™ | Day 3 C. difficile TOX A/B II ™ 20 min assay | Day 3 TOX A/B QUIK CHEK ™ |
|---|---|---|---|---|---|---|
| TL001 | + | + | + | + | + | + |
| TL002 | + | + | + | + | + | + |
| TL003 | + | + | + | + | + | + |
| TL004 | + | + | + | + | + | + |
| TL005 | + | + | + | + | + | + |
| TL006 | + | + | + | + | + | + |
| TL007 | − | − | − | − | − | − |
| TL008 | − | − | − | − | − | − |

Example 8

Use of a Method and Apparatus to Test Clinical Samples in a Clinical Lab Setting The method and apparatus used in Examples 4-7, above, were used to analyze clinical samples suspected of containing C. difficile toxins A and/or B. More specifically, an embodiment of the device of the invention, coupled with an embodiment of the method of the invention, sold together by TechLab, Inc. under the tradename TOX A/B QUIK CHEK™ (TechLab cat. no. T5033) was compared with tissue culture assays at 3 commercial clinical laboratories and by the inventors. The study sites and investigators, along with the number and source of specimens are presented in the following table. The device and method of the invention were compared to tissue culture assay because tissue culture assay is considered the "Gold Standard" for detecting C. difficile toxin in fecal samples. Discrepant results were analyzed using either the C. difficile TOX A/B II™ test or the Meridian Premier™ Toxins A&B test, both of which are microtiter ELISAs for detecting toxins A and B in fecal specimens. For studies performed by the inventors in this Example, tissue culture assay was performed using the C. Difficile TOX-B TEST assay of TechLab, Inc.

When comparing the device and method of the invention to the tissue culture assay the sensitivity, specificity, positive and negative predictive values, and percent correlation were determined. The 95% Confidence Intervals were also determined for the analysis versus tissue culture assay.

Figure 22:
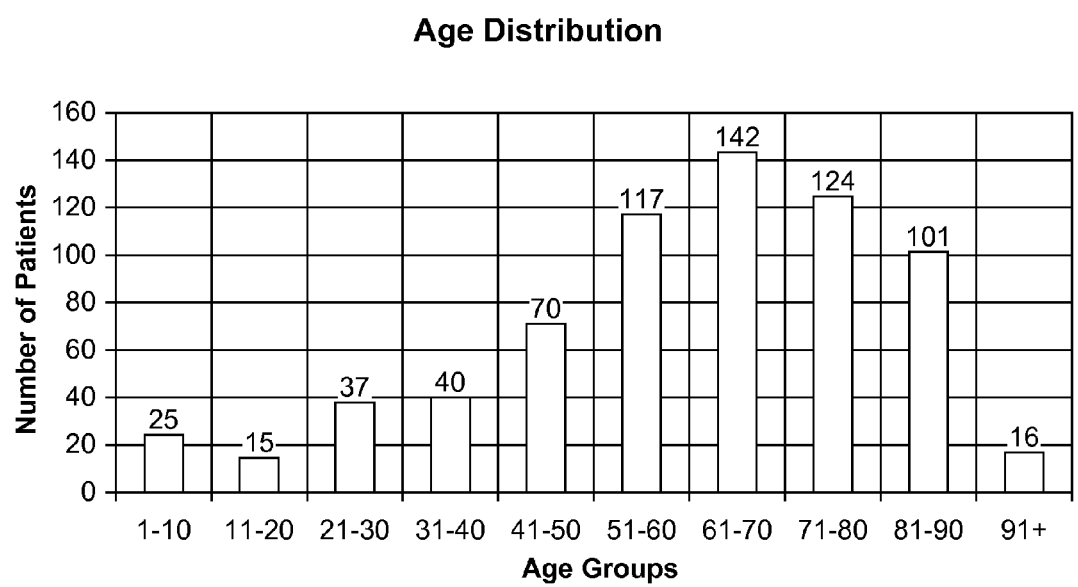
FIG. 22 depicts a table illustrating an age distribution of patients of the method of the invention.

The gender identification was available for 294 patients. There were 177 females (60.2%) and 117 males (39.8%). Age information was available for 613 patients. The age ranged from approximately 1 year to 95 years, with the distribution shown in the table illustrated in FIG. 22. The number above each bar in the table represents the number of patients who were in the specified age group.

The tables below show a summary of the clinical performance of the device and method of the invention. Results from all 5 clinical studies performed are included in the summary. Results from the device and method of the invention were compared to tissue culture assay and discrepant results were analyzed by either the C. Difficile TOX A/B II™ test (the presently discussed device and method of the invention) or the Meridian Premier™ Toxins A&B test. The results show that the TOX A/B QUIK CHEK™ test exhibited a sensitivity and specificity of 90.2% and 99.7%, respectively, compared to the tissue culture assay. The predictive positive and negative values were 98.6% and 97.9%, respectively, and the correlation was 98.0%.

TABLE 11

Summary of Clinical Performance of a Device and Method of the Invention

| n = 842 | Tissue Culture Positive Samples | |
|---|---|---|
| | | Tissue Culture Negative Samples |
| TOX A/B QUIK CHEK ™ positive | 138 | 2 |
| TOX A/B QUIK CHEK ™ negative | 15 | 687 |
| | | 95% Confidence Interval |
| Sensitivity | 90.2 | 84.1-94.2 |
| Specificity | 99.7 | 98.8-99.9 |
| Predictive Positive Value | 97.9 | 96.4-98.7 |
| Correlation | 98.0 | 97.8-98.2 |

Of the 2 tissue culture-negative/TOX A/B QUIK CHEK™-positive samples, 1 was negative in the TOX A/B II™ test. Of the 15 specimens that were tissue culture-positive/TOX A/B QUIK CHEK™-negative, 12 were negative in the C. Difficile TOX A/B II™ test or the Meridian Premier™ Toxins A&B test.

Example 9

Effect of Fecal Specimen Consistency

To further characterize the method and device of the invention, an embodiment of the device was tested with an embodiment of the method to determine the effect of fecal specimen consistency on the performance of the device and method.

The reaction of fecal specimens of varying consistencies in the TOX A/B QUIK CHEK™ test is shown in the table below.

A total of 805 fecal samples of known consistency were included in the analysis. The percentages of positive reactions using either tissue culture assay or the TOX A/B QUIK CHEK™ test were similar in all three types of fecal specimens (liquid, semi-solid, and solid). All of the specimens were submitted for *C. difficile* testing. The basis of the submission was the clinical history of the patient and not the consistency of the specimen. The results show the TOX A/B QUIK CHEK™ test performed similarly to the tissue culture assay when testing samples of different consistencies.

TABLE 12

Reaction of fecal specimens of varying consistencies in the TOX A/B QUIK CHEK ™ test

| # of Specimens (n = 805) | Liquid Specimens (n = 487) | Semi-solid Specimens (n = 294) | Solid Specimens (n = 24) |
|---|---|---|---|
| Positive by tissue culture assay | 87 (17.9%) | 56 (19.0%) | 3 (12.5%) |
| Positive by TOX A/B QUIK CHEK ™ | 76 (15.6%) | 50 (17%) | 3 (12.5) |

Example 10

Comparison of Detection of *Clostridium difficile* Glutamate Dehydrogenase Using the Device of the Invention and ELISA The device of the invention was used to detect the glutamate dehydrogenase antigen of *C. difficile* in 49 fecal samples, and the results compared to results obtained with an ELISA method. The method described in Example 1 was used to detect the toxins, with the following modifications.

Fecal samples for use in the device were diluted as specified in Example 1 with sample diluent containing antibodies (in this case specific for the glutamate dehydrogenase enzyme of *C. difficile*) that had been chemically conjugated to horseradish peroxidase detecting enzyme (conjugate). The mixed sample (300 microliters) was then applied to the application pad (wicking pad) through the hole in the device (application port) and after 15 minutes at room temperature, washing solution (saline/detergent mix) was added to the top of the membrane followed by the chemical substrate solution. The results were read visually as specified in Example 1.

The TechLab Inc. Tox A/B ELISA was used as specified in the manufacturer's product insert. Briefly, the fecal sample was diluted 1:5 in sample diluent and mixed by vortexing. Each well of the ELISA plate received 50 microliters of conjugate solution containing antibodies specific for glutamate dehydrogenase coupled to horseradish peroxidase and then 100 microliters of a mixed sample was added to each well. The plate was then incubated at 37° C. for 50 minutes to allow the antibodies attached to the microwells and antibody in the conjugate solution to bind the glutamate dehydrogenase. The wells were then washed thoroughly to remove unbound horseradish peroxidase. One hundred microliters of substrate solution was then added to each well, incubated 5 minutes, and then the reaction was stopped by adding 50 microliters of dilute acid solution. Results were read at 450 nm on an ELISA reader. Positive samples had an optical density greater than 0.12.

Table 13 shows the results of the assays, and compares the results of the method and device of the present invention with the ELISA assay.

TABLE 13

Comparison of the method and device of the invention with an ELISA Method

| N = 49 | Ag Invention Pos | Ag Invention Neg |
|---|---|---|
| *C. diff.* Chek pos | 9 | 0 |
| *C. diff.* Chek neg | 0 | 40 |
| Sensitivity | 100.0 | |
| Specificity | 100.0 | |
| Predicted Positive Value | 100.0 | |
| Predicted Negative Value | 100.0 | |
| Correlation | 100.0 | |

The results indicate that the device and method of the present invention produce results that are identical to the sensitive ELISA method used. Thus, the device and method of the invention are suitable for detection of numerous substances of interest.

It will be apparent to those skilled in the art that various modifications and variations can be made in the practice of the present method and in construction and use of the present device without departing from the scope or spirit of the invention. Other embodiments of the invention will be apparent to those skilled in the art from consideration of the specification and practice of the invention. It is intended that the specification and examples be considered as exemplary only.

The invention claimed is:

1. A device for detecting at least one substance of interest in a liquid sample, the device comprising:
    (a) a receptacle comprising a porous material for receiving the liquid sample,
    wherein the porous material is capable of absorbing and transmitting at least a portion of the liquid sample, and
    (b) a porous membrane that comprises a specific binding pair member that is specific for the substance of interest or a substance bound to the substance of interest,
    wherein the receptacle and porous membrane are each shaped to permit the porous membrane to be in direct contact with the porous material over at least a portion of the porous membrane that comprises the specific binding pair member such that the porous material is in physical contact with a bottom side of the porous membrane, and wherein the specific binding pair member is in continuous contact with the porous material to allow for continuous diffusion of the liquid sample between the porous material and the specific binding pair member, which is located directly above the porous material to which the liquid sample was applied.

2. The device of claim 1, further comprising a container containing the receptacle.

3. The device of claim 1, further comprising a holder for the porous membrane.

4. The device of claim 1, further comprising a wash solution receiving pad.

5. The device of claim 1, further comprising a liquid sample application pad.

6. The device of claim 1, further comprising a filtration pad.

7. The device of claim 1, wherein the device comprises a container containing a reaction pad comprising the porous material and the porous membrane, the container comprising a holder for the porous membrane, wherein the container causes pressure to be exerted on the porous membrane and/or the porous material such that at least a portion of the porous material is compressed.

8. A device for detecting at least one substance of interest in a liquid sample, the device comprising:

(a) a receptacle comprising a porous material for receiving the liquid sample, wherein the porous material is capable of absorbing and transmitting at least a portion of the liquid sample, and
(b) a porous membrane that comprises a specific binding pair member that is specific for the substance of interest or a substance bound to the substance of interest,
wherein the receptacle and porous membrane are each shaped to permit the porous membrane to be in direct contact with the porous material over at least a portion of the porous membrane that comprises the specific binding pair member such that the porous material is in physical contact with a bottom side of the porous membrane, wherein the specific binding pair member is in continuous contact with the porous material to allow for continuous diffusion of the liquid sample between the porous material and the specific binding pair member, which is located directly above the porous material to which the liquid sample was applied, and wherein the porous membrane and porous material are different elements having a different chemical constitution.

9. The device of claim 8, wherein the porous membrane and porous material are in physical contact such that liquid sample applied to the porous material diffuses upwards into the porous membrane.

10. The device of claim 8, wherein the porous material and porous membrane are configured in contact with each other such that the substance of interest does not need to traverse the porous membrane in a unidirectional manner for the device to detect the substance of interest.

11. The device of claim 8, wherein the porous material and porous membrane are in contact with each other in such a way to permit simple, non-directional diffusion of a liquid between the two to occur.

* * * * *